United States Patent [19]

Tyan

[11] Patent Number: 5,753,442
[45] Date of Patent: May 19, 1998

[54] METHOD FOR DETERMINING GENETIC PREDISPOSITION FOR SERONEGATIVE SPONDYLOARTHROPATHIES AND PRODUCTS USEFUL THEREFOR

[75] Inventor: Dolly B. Tyan, Los Angeles, Calif.

[73] Assignee: Cedars-Sinai Medical Center, Los Angeles, Calif.

[21] Appl. No.: 522,942

[22] Filed: Sep. 1, 1995

[51] Int. Cl.$^6$ .............................. C12Q 1/68; C07H 21/04; C12P 19/34
[52] U.S. Cl. .......................... 435/6; 435/91.2; 435/810; 536/24.31; 536/24.33; 536/24.2; 935/8; 935/78
[58] Field of Search ....................... 435/6, 91.2, 810; 536/23.1, 24.2, 24.31, 24.33; 935/8, 77, 78

[56] References Cited

U.S. PATENT DOCUMENTS 4,965,189 10/1990 Owerbach.

FOREIGN PATENT DOCUMENTS

WO 92/07956 5/1992 WIPO.

OTHER PUBLICATIONS

Adams, E. J., et al., "HLA–B16 antigens: sequence of the ST–16 antigen, further definition of two B38 subtypes and evidence for convergent evolution of B*3902," *Tissue Antigens,* 45(1):18–26 (Jan. 1995).
Careless, D. J., et al., "Etiopathogenesis of reactive arthritis and ankylosing spondylitis," *Current Opinion In Rheumatology,* 7(4):290–298 (Jul. 1995).
D'Amato, M., et al., "Characterization of a novel HLA–B27 allele (B*2709) and its association to spondyloarthropathies," *Ninth International Congress of Immunology: San Francisco, California, USA.* abst. 984 (Jul. 1995).
Lopez, J.A., et al., "Structural polymorphism and function of HLA–B27," *Current Opinion In Rheumatology,* 7:270–278 (Jul. 1995).
Lopez, J., et al., "Structure, function, and disease association of HLA–B27," *Current Opinion In Rheumatology,* 6(4):371–377 (Jul. 1994).
Bluestone, R., "HL–A Antigens in Clinical Medicine," *Disease–a–Month,* 23:1–27 (1976).
Brewerton, D.A., et al., "Acute Anterior Uveitis and HL–A 27," *The Lancet,* 994–996 (1973).
Veys, E.M., et al., "HLA and Juvenile Chronic Polyarthritis," *Tissue Antigens,* 8:61–65 (1976).
Russell, A.S., et al., "Transplantation Antigens in Crohn's Disease: Linkage of Associated Ankylosing Spondylitis with HL–Aw27," *Digestive Diseases,* 20(4):359–361 (1975).
Arnett, F.C., Jr., "The Implications of HL–A W27," *Annals of Internal Medicine,* 84(1):94–95 (1976).
Abravaya et al., Detection of Point Mutations with a Modified Ligase Chain Reaction (Gap–LCR) *Nucleic Acids Research* 23(4):675–682 (1995).
Aho et al., "HL–A Antigen 27 and Reactive Arthritis" *Lancet* 2:157 (1973).

Altschul et al., "Basic Local Alignment Search Tool" *J. Mol. Biol.* 215:403–410 (1990).
Benjamin and Parham, "Guilt by Association: HLA–B27 and Ankylosing Spondylitis" *Immunology Today* 11(4):137–141 (1990).
Breuning et al., "Subtypes of HLA–B27 Detected by Cytotoxic T Lymphocytes and Their Role in Self–Recognition" *Hum. Immunol.* 5:259–268 (1982).
Breur–Vriesendorp et al., "Subtypes of Antigen HLA–B27 (B27W and B27K) Defined by Cytotoxic T Lymphocytes: Identification of a Third Subtype (B27C) Prevelant in Oriental Populations" *Advances in Inflammation Research: The Spondyloarthropathies,* Ziff M, Cohen S.B. (eds.), Raven Press, New York 9:55–65 (1985).
Breur–Vriesendorp et al. "Distribution of HLA–B27 Subtypes in Patients with Ankylosing Spondylitis: The Disease is Associated with a Common Determinant of the Various B27 Molecules" *Ann. Rheum. Dis.* 46:353–356 (1987).
Brewerton et al., "Ankylosing Spondylitis and HL–A 27" *Lancet* 1:904–907 (1973).
Brewerton et al., "Acute Anterior Uveitis and HL–A 27" *Lancet* 2:994–996 (1973).
Brewerton et al., "Reiter's Disease and HL–A 27" *Lancet* 2:996–998 (1973).
Calin and Fries, "Striking Prevalence of Ankylosing Spondylitis in Healthy W27 Positive Males and Females" *New Engl. J. Med.* 293(17):835–839 (1975).
Calin et al., "Genetic Differences Between B27 Positive Patients with Ankylosing Spondylitis and B27 Healthy Controls" *Arthr. Rheum.* 26(12):1460–1464 (1983).
Campbell and Trowsdale, "Map of the Human MHC" *Immunology Today* 14(7):349–352 (1993).
Choo et al., "Six Variants of HLA–B27 Identified by Isoelectric Focusing" *Immunogenet.* 23:24–29 (1986).
Choo et al., "Molecular Analysis of the Variant Alloantigen HLA–B27d (HLA–B*2703) Identifies a Unique Single Amino Acid Substitution" *Hum. Immunol.* 21:209–219 (1988).
Choo et al., "A Novel HLA–B27 Allele Maps B27 Allospecificity to the Region Around Position 70 in the α1 Domain" *Journal of Immunology* 147(1):174–180 (1991).
Coppin and McDevitt, "Absence of Polymorphism Between HLA–B27 Genomic Exon Sequences Isolated From Normal Donors and Ankylosing Spondylitis Patients" *J. Immunol.* 137(7):2168–2172 (1986).
Dawkins et al., "Prevalence of Ankylosing Spondylitis and Radiological Abnormalities of the Sacroiliac Joints in HLA–B27 Positive Individuals" *J. Rheumatol.* 8:1025–1026 (1981).

(List continued on next page.)

*Primary Examiner*—Carla J. Myers
*Attorney, Agent, or Firm*—Viviana Amzel; Pretty, Schroeder & Poplawski

[57] ABSTRACT

In accordance with the present invention, there are provided isolated nucleic acids useful in diagnostic methods and kits for detecting a genetic predisposition for seronegative spondyloarthropathies.

86 Claims, No Drawings

OTHER PUBLICATIONS de Blécourt et al., "Hereditary Factors in Rheumatoid Arthritis and Ankylosing Spondylitis" *Ann. Rheum. Dis.* 20:215–220 (1961).

Grumet et al., "Monoclonal Antibody (B27M2) Subdividing HLA–B27" *Hum. Immunol.* 5:61–72 (1982).

Grumet et al., "An HLA–B Locus Probe Clarifies Endonuclease Polymorphism of Major Histocompatibility Complex Class I Genes" *Mol. Biol. Med.* 1:501–509 (1983).

Guttridge et al., "Identification of HLA–B35, B53, B18, B5, B78, and B17 Alleles by the Polymerase Chain Reaction Using Sequence–Specific Primers (PCR–SSP)" *Tissue Antigens* 44:43–46 (1994).

Hammer et al., "Spontaneous Inflammatory Disease in Transgenic Rats Expressing HLA–B27 and Human $\beta_2$m: An Animal Model of HLA–B27–Associated Human Disorders" *Cell* 63:1099–1112 (1990).

Hersh et al., "Heredity in Ankylosing Spondylitis: A Study of Fifty Families" *Amer. J. Hum. Genet.* 2:391–408 (1950).

Higgins et al., "Ankylosing Spondytitis and HLA–B27: Restriction Fragment Length Polymorphism and Sequencing of an HLA–B27 Allele from a Patient with Ankylosing Spondylitis" *Ann. Rheum. Dis.* 51:855–862 (1992).

Hill et al., "HLA Class I Typing by PCR: HLA–B27 and an African B27 Subtype" *Lancet* 337:640–642 (1991).

Hochberg et al., "Family Studies in HLA–B27 Associated Arthritis" *Medicine* 57(5):463–475 (1978).

Hoshino et al., "Polymerase chain reaction–single–strand conformation polymorphism analysis of polymorphism in DPA1 and DPB1 genes: a simple and rapid method to test histocompatibility" *HLA–1991, Proceedings of the Eleventh International Histocompatibility Workshop and Conference* 2:335–338 (1992).

Ju and Charron, "'Two–step' procedure for DRB typing using the polymerase chain reaction–restriction fragment length polymorphism method" *HLA–1991, Proceedings of the Eleventh International Histocompatibility Workshop and Conference* 2:317–319 (1992).

Khan, M.A., "An Overview of Clinical Spectrum and Heterogeneity of Spondyloarthropathies" *Rheum. Dis. Clin. N. Amer.* 18(1):1–10 (1992).

La Nasa et al., "Association of the HLA–A2, CW2, B27, S31, DR2 Haplotype with Ankylosing Spondylitis. A Possible Role of Non–B27 Factors in the Disease" *Disease Markers* 11:191–203 (1993).

LeClercq and Russell, "The Risk of Sacroiliitis in B27 Positive Persons: A Reappraisal" *J. Rheumatol.* 11:327–329 (1984).

Maclean, L., "HLA–B27 Subtypes: Implications for the Spondyloarthropathies" *Ann. Rheum. Dis.* 51:929–931 (1992).

Metzger et al., "HL–A W27 in Psoriatic Arthropathy" *Arthr. Rheum.* 18(2):111–115 (1975).

Moesmann, G., "Hereditary and Exogenous Etiological Factors in Ankylosing Spondylitis" *Acta. Rheum. Scand.* 6:144–150 (1960).

Morris et al., "HL–A W27—A Clue to the Diagnosis and Pathogenesis of Reiter's Syndrome" *N. Engl. J. Med.* 290(10):554–556 (1974).

Morris et al., "HL–A–W27—A Useful Discriminator in the Arthropathies of Inflammatory Bowel Disease" *N. Engl. J. Med.* 290(20):1117–1119 (1974).

Ness and Grumet, "New Polymorphisms of HLA–B27 and Other B Locus Antigens Detected by RFLP Using a Locus–Specific Probe" *Hum. Immunol.* 18:65–73 (1987).

O'Connell, D., "Heredity in Ankylosing Spondylitis" *Ann. Intern. Med.* 50:1115–1121 (1959).

Olerup and Zetterquist, "HLA–DRB1 typing by polymerase chain reaction amplification with sequence–specific primers: post–amplification processing in less than 20 minutes" *HLA–1991, Proceedings of the Eleventh International Histocompatibility Workshop and Conference* 2:315–317 (1992).

Orita et al., "Rapid and Sensitive Detection of Point Mutations and DNA Polymorphisms Using the Polymerase Chain Reaction" *Genomics* 5:874–879 (1989).

Rubin et al., "Investigating the Genetic Basis for Ankylosing Spondylitis" *Arthr. Rheum.* 37(8):1212–1220 (1994).

Santamaria et al., "Sequence–Based HLA 'Typing': Direct Sequencing of Class I and Class II Genes" *HLA–1991, Proceedings of the Eleventh International Histocompatibility Workshop and Conference* 2:342–346 (1992).

Schlosstein et al., "High Association of an HL–A Antigen, W27, with Ankylosing Spondylitis" *N. Engl. J. Med.* 288(14):704–706 (1973).

Seager et al., "Evidence for a Specific B27–Associated Cell Surface Marker on Lymphocytes of Patients with Ankylosing Spondylitis" *Nature* 277:68–70 (1979).

Seeman et al., "Gene Conversion–Like Mechanisms May Generate Polymorphism in Human Class I Genes" *EMBO J.* 5(3):547–552 (1986).

Sooknanan and Malek, "NASBA: A Detection and Amplification System Uniquely Suited for RNA" *Bio/Technology* 13:563–564 (1995).

Spencer et al., "Ankylosing Spondylitis—the Role of HLA–B27 Homozygosity" *Tissue Antigens* 14:379–384 (1979).

Steere et al., "Use of DNA Probes from the 5' Flanking Region of the HLA–B Gene to Examine Polymorphism at the HLA–B Locus" *Human Immunology* 16:137–147 (1986).

Szöts et al., "Complete Sequence of HLA–B27 cDNA Identified Through the Characterization of Structural Markers Unique to the HLA–A, –B, and –C Allelic Series" *Proc. Natl. Acad. Sci. USA* 83:1428–1432 (1986).

Taidi–Laskowski et al., "Use of RecA Protein to Enrich for Homologous Genes in a Genomic Library" *Nuc. Acids Res.* 16(16):8157–8169 (1988).

Taurog et al., "Susceptibility to Inflammatory Disease in HLA–B27 Transgenic Rat Lines Correlates with the Level of B27 Expression" *Journal of Immunology* 150(9):4168–4178 (1993).

Tiercy et al., "Oligonucleotide Typing Analysis of the Polymorphism of DRB1 and DRB3 Genes Within DRw52 Haplotypes" *Immunobiology of HLA* Springer Verlag, New York II:248–250 (1989).

Tiwari and Terasaki eds., "Reiter's Disease" *HLA and Disease Association* Springer–Verlag, New York 107–109 (1985).

Trapani et al., "A 3.5 Kilobase Taq I Restriction Fragment of Genomic DNA Segregates with HLA–B27" *Immunogenetics* 21:189–192 (1985).

Trapani et al., "Molecular Cloning and Partial Nucleotide Sequence of a 3.5 kb HLA–B27–Associated Fragment of Genomic DNA" *Immunogenetics* 22:399–405 (1985).

van der Linden et al., "The Risk of Developing Ankylosing Spondylitis in HLA-B27 Positive Individuals" *Arthr. Rheum.* 27(3):241-249 (1984).

Verjans et al., "Restriction Fragment Length Polymorphism of the Tumor Necrosis Factor Region in Patients with Ankylosing Spondylitis" *Arthritis and Rheumatism* 34(4):486-489 (1991).

Vilches et al., "Nucleotide Sequence of HLA-B *2706" *Immunogenetics* 39:219 (1994).

Weiss et al., "Organization, Sequence and Expression of the HLA-B27 Gene: A Molecular Approach to Analyze HLA and Disease Associations" *Immunobiol.* 170:367-380 (1985).

Weiss et al., "Molecular Biology of the HLA-B27 Locus" *Br. J. Rheumatol.* 27(Suppl II):12-18 (1988).

Woodrow and Eastmond, "HLA B27 and the Genetics of Ankylosing Spondylitis" *Ann. Rheum. Dis.* 37:504-509 (1978).

Yap et al., "Nonisotopic SSCP Detection in PCR Products by Ethidium Bromide Staining" *Trends in Genetics* 8(2):49 (1992).

METHOD FOR DETERMINING GENETIC PREDISPOSITION FOR SERONEGATIVE SPONDYLOARTHROPATHIES AND PRODUCTS USEFUL THEREFOR

BACKGROUND OF THE INVENTION

FIELD OF THE INVENTION

The present invention relates to diagnostic methods and isolated nucleic acid fragments useful therefor. In a particular aspect, invention diagnostic methods are employed for determining a predisposition for seronegative spondyloarthropathies.

DESCRIPTION OF THE BACKGROUND

Ankylosing spondylitis (AS) is the prototype for a variety of diseases known as the seronegative spondyloarthropathies (Khan, M. A. Rheum *Dis Clin N Amer* 18:1–10 (1992)). Other diseases in this group include Reiter's syndrome (RS), reactive arthritis, and other inflammatory diseases such as psoriatic arthritis, arthritis associated with inflammatory bowel disease, and acute anterior uveitis (AAU). The etiologies of all are unknown, except that the inclusion of reactive arthritis/post-dysenteric RS in this group suggests that an infectious insult is involved.

The seronegative spondyloarthropathies are characterized in the early stages by a chronic inflammatory infiltrate containing lymphocytes and plasma cells and later by fibroblastic proliferation, leading to formation of scar tissue as a chronic healing process ensues. The scarring results in the ankylosis of joints which may then undergo enchondral ossification of non-inflamed articular cartilage. The tendency of the fibrous tissue to ossify produces radiographic changes such as paravertebral ossification, bamboo spine, and plantar spurs. Inflammation which begins within the cartilage can involve the periosteum, ligaments, joint capsules, annulus of the intervertebral disks, synovium, as well as the uveal tract and aortic wall. The main extra-skeletal manifestations include iritis and chronic aortitis leading to aortic regurgitation. In addition to lone aortic regurgitation, atrioventricular conduction abnormalities can also occur requiring valve replacement or pacemaker treatment, respectively.

Ankylosing spondylitis (AS) is an axial inflammation of unknown etiology which, if untreated, leads to fusion of the spinal vertebrae and the phenotype known as "bamboo spine." Thus, AS is characterized clinically by: (1) limitation of motion of the lumbar spine in all three planes—anterior flexion, lateral flexion, and extension, (2) history of or the presence of pain at the dorso-lumbar junction or in the lumbar spine, and (3) limitation of chest expansion to 1 in. (2.5 cm) or less, measured at the level of the fourth intercostal space.

Reiter's syndrome is a post-venereal or post-dysenteric disease. It is considered to be present when there is a classic triad of nonspecific urethritis, conjunctivitis, and arthritis. The arthritis is usually asymmetric and oligoarticular involving the lower extremities. Frequent associated symptoms include sausage digits; mucocutaneous lesions such as keratoderma blennorrhagica, oral ulcers, balanitis; heel pain; and rapid weight loss.

B27 is a typical Major Histocompatibility Complex (MHC) Class I molecule encoded by a gene with 7–8 exons corresponding to the leader, α1, α2, α3, transmembrane, two cytoplasmic domains, and a possible third cytoplasmic domain contiguous with the 3' untranslated (3'UT) region (Weiss et al. *Immunobiol* 170:367–380 (1985)). An exceptionally strong association between the HLA-B locus antigen, previously known as w27, and ankylosing spondylitis has been noted (Schlosstein et al. *N Engl J Med* 288:704–706 (1973) and Brewerton et al. *Lancet* 1:904–907 (1973)). While the frequency of the B27 allele (as it is now known) was 4–8% in the general population, 88–96% of AS patients were positive for this antigen. In quick succession, associations between B27 and other seronegative spondyloarthropathies were reported showing B27 frequencies of 76–96% in RS (Brewerton et al. *Lancet* 2:996–998 (1973) and Morris et al. *N Engl J Med* 290:554–556 (1974)), 60–94% in reactive arthritis (Aho et al. *Lancet* 2:157 (1973) and Aho et al. *Ann Rheum Dis* 34(Suppl)L:29–30 (1975)), 52–58% in AAU (Brewerton et al. *Lancet* 2:994–996 (1973) and Brewerton, D.A. *Ann Rheum Dis* 34(Suppl):33–35 (1975)), and lower but significant increases in psoriatic arthritis (Metzger et al. *Arthr Rheum* 18:111–115 (1975)) or inflammatory bowel disease patients (Morris et al. *N Engl J Med* 290:1117–1119 (1974)). Many studies have subsequently confirmed these associations, demonstrating that they cross racial and ethnic lines (reviewed in Tiwari and Terasaki, *HLA and Disease Association*, Springer-Verlag New York (1985)). For example, in Japan where the B27 allele frequency is only 1% in the general population, 81% of AS patients are B27 positive, a frequency similar to that seen in Caucasian patients. While the presence of the B27 allele is elevated in Black AS patients, only 58% of these patients are positive for B27 compared to 4% of Black controls.

Despite the large number of studies showing a high prevalence of B27 in affected individuals, the prevalence of disease in the general population or in B27+ individuals remains controversial. Very large population studies done prior to the association with B27 put the prevalence of AS in the overall (Caucasian) population between 1 in 2000 (0.05%) and 2% (Hersh et al. *Amer J Hum Genet* 2:391–408 (1950) and Moesmann, G. *Acta Rheum Scand* 6:144–150 (1960)). Family members (blood relatives) of AS positive probands (i.e., first subject of a family studied), on the other hand, had a prevalence of AS ranging from 2.8 to 30%, increasing the risk to blood relatives between 22.6 and 100-fold (O'Connell, D. *Ann Intern Med* 50:1115–1121 (1959), Hersh et al. *Amer J Hum Genet* 2:391–408 (1950), deBlecourt et al. *Ann Rheum Dis* 20:215–220 (1961), and Moesmann, G. *Acta Rheum Scand* 6:144–150 (1960)).

Subsequent to the description of the B27/AS association, B27+ individuals were studied to determine their prevalence of AS compared to the general population. The results were discordant and controversial, with reports of AS in the B27+ population ranging from 1.6% to 26% (Calin and Fries *N Engl J Med* 293:835–839 (1975) and Dawkins et al. *J Rheumatol* 8:1025–1026 (1981)). It was also suggested that underdiagnosis occurs up to 80% of the time, perhaps accounting for the lower frequencies previously reported. Family studies of AS positive probands were also repeated and between 10.6% and 35% were found to be affected (van der Linden et al. *Arthr Rheum* 27:241–249 (1984), Hochberg et al. *Medicine* 57:467–475 (1978), Calin and Fries *N Engl J Med* 293:835–839 (1975), Woodrow and Eastmond *Ann Rheum Dis* 37:504–509 (1978), and LeClercq and Russell *J Rheumatol* 11:327–329 (1984)). In most cases, the affected family members were B27+ and the risk to B27+ family members calculated to be 10 to 20-fold higher than to B27+individuals in the general population.

In contrast, B27 negative probands suffering from AS had affected relatives who were B27 negative as well (Hochberg et al. *Medicine* 57:467–475 (1978)). Finally, in families of B27+ individuals without disease. AS was found in only 1.9% of the B27+ relatives (Calin et al. *Arthr Rheum* 26:1460–1464 (1983)), a prevalence similar to that found in the general population. Despite the wide variation in frequency of disease in the various groups studied, the general consensus is that AS has a prevalence of about 0.2% in the random population, 2% in the B27+ population, and 20% in B27+ relatives of an AS proband (Khan, M. A. *Rheum Dis Clin N Amer* 18:1–10 (1992)). Thus, since B27+ relatives of AS patients are 10 times more likely to acquire disease, methods of predicting this susceptibility are clearly desired.

Early attempts to address these questions centered around the search for polymorphism in the B27 genes to determine whether those derived from AS patients were different from those found in unaffected B27+ controls. In 1982 (Grumet et al. *Hum Immunol* 5:61–72 (1982)), a monoclonal antibody (B27M2) was produced capable of subdividing B27+ individuals into positive and negative, and eventually intermediate groups. In collaboration with groups who were using bulk Cytotoxic T-lymphocytes (CTLs) to assess B27 heterogeneity, it was demonstrated that their respective CTL subtypes (three each) corresponded to the subtypes distinguished by the anti-B27 monoclonal antibody (Breuning et al. *Hum Immunol* 5:259–268 (1982) and Breur-Vriesendorp et al. *In Advances in Inflammation Research Vol.* 9:55–65 The Spondyloarthropathies. Ziff M, Cohen S. B. (eds.), Raven Press, New York (1985)). Subsequently, using an IEF (isoelectric focussing) system, (Choo, et al. *Immunogenet* 23:24–29 (1986)), described six B27 variants.

Amino acid and nucleotide sequencing of B27 have revealed the molecular basis of the heterogeneity at the B27 allele. Eight B27 allelic variants are now known, which are the result of alterations in 13 residues, all located in the first and second external domains (i.e., exons 2 and 3). It should be noted that no particular B27 subtype correlates with the presence of disease (Breur-Vriesendorp et al. *Ann Rheum Dis* 46:353–356 (1987) and Maclean, L. *Ann Rheum Dis* 51:929–931 (1992)). In fact, B*2701, B*2702, B*2704, B*2705, and B*2706 are all known to be associated with disease, whereas B*2707 and B*2708 have been found too infrequently to draw a conclusion of disease correlation. B*2703 is found only in the Black population and at low frequency. It was described as being found only in unaffected individuals (Hill et al. *Lancet* 337:640–642 (1991)); however, no AS patients were studied. This, together with its low frequency, precludes conclusions regarding its role in disease susceptibility or resistance.

In addition to the B27 subtyping studies, several studies have compared the B27 gene sequences of AS patients versus non-patients to attempt to discern variations in coding sequences which would predispose to disease (Coppin and McDevitt *J Immunol* 137:2168–2172 (1986), Weiss et al. *Br J Rheumatol* 27(Suppl II):12–18 (1988), and Higgins et al. *Ann Rheum Dis* 51:855–862 (1992)). All have been unsuccessful in demonstrating any differences. Furthermore, these studies do not address the question of whether there is a gene closely linked to B27 which is responsible for disease susceptibility. A new study showing linkage between the Major Histocompatibility Complex and Ankylosing Spondylitis (Rubin et al. *Arthr Rheum* 37:1212–1220 (1994)) does not resolve the controversy since the highest log of the odds (LOD) score occurs at a recombination frequency (θ)=0.05.

Other investigators have looked at genes flanking B27 in the hope of finding a more strongly associated marker. No other class I genes have been found within 6 kb 5' or 30 kb 3' of the B27 gene (Weiss et al. *Immunobiol* 170:367–380 (1985)). In addition, no association has been found with Class II, nor with the almost adjacent TNF or HLA-C loci other than secondary associations due to linkage disequilibrium, a well known feature of the MHC. Thus, the basis for the associations remains unknown, and no "disease susceptibility" genes or genetic markers have been identified, until the present invention, despite intensive study worldwide.

Thus, it would be desirable to have a method to identify which B27+ individuals are generally predisposed to develop a seronegative spondyloarthropathy. Up to now, there has been no way to distinguish B27+ normal individuals from either B27+ diseased individuals or B27+ individuals predisposed to disease.

SUMMARY OF THE INVENTION

The present invention provides isolated nucleic acids which may be used as probes or primers in diagnostic assays for detecting a genetic predisposition for developing seronegative spondyloarthropathies.

The present invention also provides methods for detecting whether a subject has genetic predisposition for developing a seronegative spondyloarthropathy. The invention methods are particularly useful as they permit the distinction of B27+ normal subjects who are resistant to seronegative spondyloarthropathies from B27+ normals who are susceptible (but as yet unaffected) to such disease.

The present invention additionally provides diagnostic systems, preferably in kit form, comprising at least one invention nucleic acid in a suitable packaging material. The invention diagnostic kits are useful for detecting the existence of a genetic predisposition for a seronegative spondyloarthropathy in a subject.

DETAILED DESCRIPTION OF THE PREFERRED EMBODIMENTS OF THE INVENTION

The present invention provides a method for detecting the genetic predisposition of a subject to develop seronegative spondyloarthropathies. In one embodiment the invention method comprises detecting, in a subject, the absence of the cytosine nucleotide in the 3' flanking region of an HLA-B gene at a position corresponding to nucleotide 4495 of SEQ ID NO:1.

In accordance with the present invention, it has been demonstrated that the absence of a cytosine nucleotide (e.g., the presence of an adenine, guanine or thymine) at the genomic position corresponding to nucleotide 4495 of SEQ ID NO:1 correlates with a predisposition for a variety of diseases referred to as seronegative spondyloarthropathies. Thus, by detecting the existence of such a sequence in a particular subject, medical practitioners are provided with valuable diagnostic information.

As used herein, the phrase "genetic predisposition" refers to the increased likelihood that a given subject, having a particular genomic or transcribed nucleic acid sequence, will develop a certain disease or diseases. In accordance with the present invention, it has been found that the absence of the cytosine nucleotide in either genomic DNA or cDNA (or the absence of a guanine nucleotide in the RNA), corresponding to nucleotide 4495 of SEQ ID NO:1 correlates with an increased susceptibility (e.g., at least 2-fold increase) for developing a seronegative spondyloarthropathy. In a preferred embodiment of the invention, the occurrence of this particular sequence correlates with at least a 3-fold, preferably a 5-fold, more preferably a 7-fold, yet more preferably a 10-fold, increase in susceptibility for developing a seronegative spondyloarthropathy. Since the absence of a cytosine ("C") nucleotide at a position corresponding to 4495 of SEQ ID NO:1 has the same correlation to seronegative spondyloarthropathy disease susceptibility as the presence of adenine, guanine or thymine nucleotides at a position corresponding to 4495 of SEQ ID NO:1, methods for detecting the presence of adenine, guanine, or thymine, preferably adenine, at a nucleotide position corresponding to 4495 of SEQ ID NO:1 are also contemplated herein.

As used herein, the phrase "seronegative spondyloarthropathies" refers to a related group of diseases, such as, Ankylosing spondylitis (AS), Reiter's syndrome (RS), reactive arthritis, and other inflammatory diseases such as psoriatic arthritis, arthritis associated with inflammatory bowel disease, chronic juvenile arthritis, acute anterior uveitis (AAU), and the like.

As used herein, the phrase "the 3' flanking region of an HLA-B gene" refers to the genomic region that is 3' downstream of the 3' untranslated region of an HLA-B gene, preferably the HLA B27 gene. For example, the 3' untranslated region of the HLA B27 gene consensus sequence set forth in SEQ ID NO:1 terminates at nucleotide 3967. Thus, the 3' flanking region of the B27 gene corresponds to nucleotides 3968–6653 of SEQ ID NO:1.

Numerous methods for detecting a single nucleotide anomaly in genomic or transcribed nucleic acid sequences are well-known in the art. The present invention is not limited by any particular method used to detect the diagnostic sequences disclosed herein. For example, the pertinent sequence can be detected using a procedure selected from: polymerase chain reaction-restriction fragment length polymorphism (PCR-RFLP) (e.g., Ju et al., *New Methods of DNA Typing* "HLA-1991, Proceeding of the Eleventh International Histocompatibility Workshop and Conference" Vol. 2, 1992, pgs 317-319); ligase chain -reaction (LCR) (see, e.g., Abravaya et al., 1995, NAR, 23(4):675–682); oligotyping using Sequence Specific Primers (SSP) (e.g., Olerup et al., *New Methods of DNA Typing* "HLA-1991, Proceedings of the Eleventh International Histocompatibility Workshop and Conference" Vol. 2, 1992, pgs 315–317); oligotyping using Sequence Specific Oligonucleotide Probes (SSOP) (Tiercy et al., *Immunobiology of HLA*, Vol. II, pp. 248–250, 1987, Springer Verlag, New York); Single-stranded conformation polymorphism (SSCP) (Yap et al., Feb/1992, *Trends in Genetics*, 8(2):49; and Orita et al., 1989, *Genomics*, 5:874–879); direct sequencing of the 3' flanking region of the HLA-B locus gene (see, e.g., Santamaria et al., *New Methods of DNA Typing* "HLA-1991, Proceedings of the Eleventh International Histocompatibility Workshop and Conference Vol. 2, 1992, pgs 342-345); and the like.

The presence of either adenine, guanine, or thymine nucleotides at a position corresponding to nucleotide 4495 of SEQ ID NO:1 correlates to the absence of cytosine at a position corresponding to nucleotide 4495, and to the presence of -TAGA-, -TGGA- or -TTGA- sequence, respectively, at nucleotides corresponding to nucleotides 4494–4497 of SEQ ID NO:1, or in the alternative, the absence of the TaqI restriction enzyme sequence "TCGA" at this position. Thus, methods for detecting any one of these particular sequences in the 3' flanking region of an HLA-B-locus gene are also contemplated herein for detecting a genetic predisposition for seronegative spondyloarthropathies. The particular -TAGA-, -TTGA-, -TGGA- or -TCGA- sequence detected by the invention method lies within 2 kb downstream of the genomic DNA corresponding to the 3' terminus of the 3' untranslated region of the HLA-B gene. In a preferred embodiment, the particular sequence detected by the invention method lies within 1.5 kb, more preferably within 1 kb, downstream of the genomic DNA corresponding to the 3' terminus of the 3'untranslated region of the HLA-B gene.

A presently preferred method for detecting the absence of the sequence -TCGA- in the 3' flanking region of the HLA-B locus is to isolate transcribed RNA from a particular subject, amplify the region surrounding a nucleotide corresponding to position 4495 of SEQ ID NO:1 (using, for example, one of the primer pairs in Table 1, such as F3/R3), and subsequently contact the amplification product with TaqI restriction enzyme. If the complete undigested amplification product is observed, then no TaqI site (-TCGA-) is present, which correlates with a predisposition to seronegative spondyloarthropathies. However, observance of a digested amplification product indicates the presence of a TaqI site, which correlates with lack of susceptibility to seronegative spondyloarthropathies.

The invention method is particularly advantageous in subjects that are known to have the B27 allele (i.e., B27+ ). The invention method permits the distinction of B27+ normals who are resistant to disease from B27+ normals who are susceptible to disease (but as yet unaffected thereby), such as seronegative spondyloarthropathies. In these subjects, genomic DNA or cDNA derived from a subject's mRNA is amplified and analyzed for the diagnostic sequences described above.

In addition, blood relatives of known B27 positive individuals and/or known AS patients are more suitable for analysis with the invention diagnostic method. For example, when invention methods are carried out on blood relatives of AS patients, the presence of an amplification product using invention nucleic acids identifies who is B27+ and TaqI digestion of the amplification product distinguishes who is at risk for Ankylosing spondylitis. Therefore, invention methods are also advantageously useful for detecting, using a single assay in previously undiagnosed subjects, whether an individual is B27+ and simultaneously whether the individual is susceptible to disease. For example, the absence of an amplification product when the primer pair F3/R3 (set forth in Table 1) is employed indicates that the particular subject does not contain the B27 allele (i.e. is B27-).

In addition, the 3' flanking region of the B27 gene may be transcribed as part of mRNA encoding a protein other than the B27 antigen. For example, in accordance with the present invention, it has also been discovered that a novel open reading frame encoded by mRNA transcribed from nucleotides corresponding to nucleotides 4112–4556 of SEQ ID NO:1 is diagnostic for genetic predisposition for seronegative spondyloarthropathies. This transcribed region may be part of an alternatively spliced B27 coding sequence or a different closely linked gene. However, the presence of the fully transcribed region from nucleotides corresponding to nucleotides 4270–4556 of SEQ ID NO:1 has only been detected in B27+ individuals, and not in B27 negative individuals.

Thus, in a preferred embodiment, the invention method comprises:

detecting in a subject a transcribed nucleic acid sequence, in whole or in part, corresponding to nucleotides 4112–4556, inclusive, of SEQ ID NO:1.

In a preferred embodiment for detecting said transcribed sequence, the PCR-RFLP method is employed (e.g., Ju et al., *New Methods of DNA Typing* "HLA-1991, Proceedings of the Eleventh International Histocompatibility Workshop and Conference" Vol. 2, 1992, pgs 317–319). Thus, the invention method contemplates:

a) contacting nucleic acid obtained from a subject suspected of having a seronegative spondyloarthropathy with primers that amplify a detectable nucleic acid fragment of SEQ ID NO:1 containing nucleotide corresponding to nucleotide 4495 of SEQ ID NO:1, under conditions suitable to form a detectable amplification product; and b) determining whether the amplification product is susceptible to digestion by TaqI restriction enzyme, whereby absence of digestion indicates that said subject has a genetic predisposition for a seronegative spondyloarthropathy. This particular method is carried out essentially as described in Example III, described hereinafter.

As used herein, the phrase "conditions suitable to form a detectable amplification product" refers to the conditions that provide an amplification product that is long enough to be detected using well-known detection means, such as, for example, visually, with an appropriate probe, or using a restriction enzyme (such as TaqI). Typically, the length of the amplification product will be at least 50 nucleotides in length, preferably at least 75, more preferably at least 100, with amplification products of at least 200 nucleotides in length being especially preferred. For example, see Table 1 for a list of primer pairs that produce detectable amplification products ranging from 50 nucleotides up to over 400 nucleotides in length.

In accordance with another embodiment of the present invention, there are provided isolated nucleic acids comprising at least 5 contiguous nucleotides derived from nucleotides 4112–4556 (inclusive) of SEQ ID NO:1. In preferred embodiments of the present invention, the isolated nucleic acids comprise at least 10, more preferably at least 15, yet more preferably at least 20, contiguous nucleotides derived from nucleotides 4112–4556 (inclusive) of SEQ ID NO:1, with at least 30 contiguous nucleotides being especially preferred. Invention nucleic acids can be in either single-stranded or double-stranded form. In one embodiment, invention nucleic acids are single-stranded oligonucleotide primers capable of amplifying (using a variety of methods well-known in the art) a nucleic acid sequence within 4112–4556 of SEQ ID NO:1. In a preferred embodiment, the amplification product contains the nucleotide corresponding to position 4495 of SEQ ID NO:1.

The skilled artisan can readily make numerous other oligonucleotide primers, within nucleotides 4112–4556 of SEQ ID NO:1, that will hybridize with and/or amplify the relevant portion of SEQ ID NO:1. For example in one embodiment of the present invention, invention nucleic acids comprise at least a pentamer oligonucleotide selected from the group of oligonucleotides represented by the formula:

N through N+4, wherein N represents any one of nucleotides 4112, 4113, 4114, . . . through nucleotide 4552 of SEQ ID NO:1.

In another embodiment, invention nucleic acids comprise at least a decamer oligonucleotide selected from the group of oligonucleotides represented by the formula:

N through N+9, wherein N represents any one of nucleotides 4112, 4113, 4114, . . . through nucleotide 4547 of SEQ ID NO:1.

In an additional embodiment, invention nucleic acids comprise at least a pentadecamer oligonucleotide selected from the group of oligonucleotides represented by the formula:

N through N+14, wherein N represents any one of nucleotides 4112, 4113, 4114, through nucleotide 4542 of SEQ ID NO:1.

In yet another embodiment, invention nucleic acids comprise at least a 20 mer oligonucleotide selected from the group of oligonucleotides represented by the formula:

N through N+19, wherein N represents any one of nucleotides 4112, 4113, 4114, . . . through nucleotide 4537 of SEQ ID NO:1.

In still another embodiment, invention nucleic acids comprise at least a 30 mer oligonucleotide selected from the group of oligonucleotides represented by the formula:

N through N+29, wherein N represents any one of nucleotides 4112, 4113, 4114, . . . through 4527 of SEQ ID NO:1.

Particularly preferred oligonucleotides contemplated by the present invention, which are useful as primers in the diagnostic assays described herein, include primers selected from: F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), GRAIL-R (SEQ ID NO:8), and the like.

Invention oligonucleotides are useful in the diagnostic methods described herein, as probes for detecting a particular sequence, as primers in various amplification protocols, and the like. Isolated nucleic acids derived from nucleotides corresponding to nucleotides 4112–4556 of SEQ ID NO:1 can be produced using methods well-known in the art, such as oligonucleotide synthesis using standard DNA synthesizers, PCR amplification, recombinant cloning techniques, and the like.

In another embodiment of the present invention, isolated nucleic acid comprising the entire nucleic acid sequence set forth as nucleotides corresponding to nucleotides 4112–4556, inclusive, of SEQ ID NO:1 is contemplated. Another preferred nucleic acid of the invention comprises nucleotides corresponding to nucleotides 4270–4556, inclusive, of SEQ ID NO:1. These invention nucleic acids can be produced synthetically, as discussed above, using PCR amplification with appropriately selected primers, or using other methods well-known in the art.

As employed herein, the phrase "substantially the same nucleotide sequence" refers to DNA having sufficient homology to the reference polynucleotide, such that it will hybridize to the reference nucleotide under typical moderate stringency conditions. In one embodiment, DNA having "substantially the same nucleotide sequence" as the reference nucleotide sequence has at least 60% homology with respect to the nucleotides 4270–4556, inclusive, of SEQ ID NO:1 or nucleotides 4112–4556, inclusive, SEQ ID NO:1. DNA having at least 70%, more preferably 80%, yet more preferably 90%, homology to the reference nucleotide sequence is preferred.

Since it has been demonstrated that the nucleic acid sequence set forth as nucleotides 4112–4556 of SEQ ID NO:1 is part of a coding region (cDNA), the invention nucleic acid corresponding to nucleotides 4112–4556 of SEQ ID NO:1 can also be isolated as part of a larger transcribed RNA or cDNA sequence encoding a particular protein. Methods for isolating full-length cDNA encoding a particular protein, from a cDNA library, using known partial cDNA sequences (such as nucleotides 4112–4556 of SEQ ID NO:1) as probes are well-known in the art. For example, one of skill in the art can employ nucleotide probes derived from nucleotides corresponding to nucleotides 4112–4556 of SEQ ID NO:1 for hybridization screening of a particular cDNA library or other cDNA libraries derived from cells believed to express the corresponding full-length cDNA sequence, e.g., peripheral blood lymphocytes (PBL), brain, pituitary, immune, gonadal, adrenal, placental, and the like.

Hybridization refers to the binding of complementary strands of nucleic acid (i.e., sense:antisense strands or probe:target-DNA/RNA) to each other through hydrogen bonds, similar to the bonds that naturally occur in chromosomal DNA. Stringency levels used to hybridize a given probe with target-DNA can be readily determined by those of skill in the art. For example, moderately stringent conditions are conditions equivalent to hybridization in 50% formamide, 5X Denhart's solution, 5X SSPE, 0.2% SDS at 42° C., followed by washing in 0.2X SSPE, 0.2% SDS, at 65° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

In accordance with another embodiment of the present invention, there are provided diagnostic systems, preferably in kit form, comprising at least one invention nucleic acid in a suitable packaging material. Invention diagnostic systems are useful for assaying for the presence or absence of the nucleotide sequence -TCGA- in either genomic DNA corresponding to the 3' flanking region of the HLA-B gene locus as described herein, or in transcribed nucleic acid (such as mRNA or cDNA) set forth as nucleotides corresponding to nucleotides 4112–4556 of SEQ ID NO:1, and the like. The absence of the nucleotide sequence -TCGA- in this particular region indicates a genetic predisposition for seronegative spondlyoarthropathies.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence in the region of genomic DNA which is 3' of the HLA-B locus (preferably B27), thereby diagnosing the presence or absence of a predisposition for seronegative spondyloarthropathies. In addition, the packaging material contains instructions indicating how the materials within the kit are employed both to detect a particular sequence and diagnose a predisposition for seronegative spondyloarthropathies.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

EXAMPLES

Unless otherwise stated, the present invention was performed using standard procedures, as described, for example in Maniatis et al., *Molecular Cloning: A Laboratory Manual*, Cold Spring Harbor Laboratory Press, Cold Spring Harbor, New York, USA (1982); Sambrook et al., *Molecular Cloning: A Laboratory Manual* (2 ed.), Cold Spring Harbor Laboratory Press, Cold Spring Harbor, New York, USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

EXAMPLE 1

Genomic Cloning and Subcloning

Genomic DNA was isolated from 3 B27+ Caucasian individuals who, on the basis of extensive clinical history and/or pelvic X-rays, had previously been confirmed to be clinically normal (2.5 kb TaqI fragment) or affected with AS (3.5 kb TaqI fragment). Patient HS (A2,A25;B8,B27;Bw4, Bw6;Cwl,Cw7) was a verified unaffected 65 year old female. Patient GV (A1,A31;B8,B27;Bw4,Bw6;Cw2,Cw-) was a 42 year old male with confirmed AS. Patient DL (A2,A3;B18,B27,Bw4,Bw6;Cwl,Cw-) was a 28 year old male with confirmed absence of disease and a negative family history. The cloning procedure is described in detail in, for example, Taidi-Laskowski et al. *Nuc Acids Res* 16:8157–8169 (1988). The B27 genes (contained on EcoRI fragments) from HS, GV, and DL were cloned into the vector λgt.wes. Each individual was heterozygous for their clearly distinguishable B locus restriction fragment length polymorphisms (RFLPs). These RFLPs, together with our B locus specific probe, EI7 (Grumet et al. *Mol Biol Med* 1:501–509 (1983)), under stringent conditions (0.1X SSC, 0.1% SDS, 65° C. X 45 min X 2) were used to identify B27 clones, which were also confirmed by restriction mapping and sequencing. HS and DL had 2.5 kb RFLPs associated with their B27 genes whereas GV had a 3.5 kb associated RFLP. The B27 genes from each of these individuals was then subcloned into the 2961 bp Bluescript (KS+) phagemid vector (Stratagene) and transformed into XL-1 Blue competent cells (Stratagene). The competent cells were plated on LB-Amp plates containing IPTG and X-gal by standard procedures, and white colonies selected.

Minipreps were prepared according to standard procedures and the presence of the B27+ insert confirmed by restriction digests with HindIII, BstEII, EcoRI, and TaqI.

EXAMPLE 2

RNA Preparation

Total RNA was extracted from ~$10^8$ peripheral blood lymphocytes (PBL) or lymphoblastoid cell lines (LCL) using RNeasy (Qiagen) kits according to the manufacturer's instructions. After extraction, the RNA was treated with 3 U/μg of DNase I (RNase-free, Boehringer Mannheim) for 30 min at 37° C. and then extracted once each with $H_2O$-saturated phenol and phenol/chloroform/isoamyl alcohol (24:24:1) as described in Sun, L. and Pettinger, W. A. *Focus* 15:70–71 (1994).

EXAMPLE 3

Southern Blots

Southern blots were performed as described in, Ness D. B. and Grumet F. C. *Hum Immunol* 18:65–73 (1987), except that crosslinking by exposure to short wave length (254nm) UV for 20 seconds was used instead of baking at 80° C. for 2 hrs and probe labeling was performed using random priming (Multiprime DNA Labelling System, Amersham). Probes were routinely labelled to about $2 \times 10^9$ cpm/μg using $\alpha$-$^{32}$p -dCTP (3000 Ci/mmol).

EXAMPLE 4

Northern Blots

Total RNA Northern Blots: 10 μg total RNA originating from different PBL or LCL samples were run on 1% agarose gels with formaldehyde according to standard procedures and blotted as described for Southerns, with a UV crosslinking time of 30 sec. Washes were performed twice in 2X SSC, 0.1% SDS at room temperature for 5 min. each, and then twice in 0.1X SSC, 0.1% SDS at 62° C. for 45 min. each.

PolyA+ Northern Blots: A Multiple Tissue Northern blot (Human II, Clontech) containing 3 μg/lane polyA+RNA was also employed and used according to the manufacturer's instructions. Wash conditions were essentially identical to those used for the total RNA Northern. According to the product information, the samples/#donors used for this Northern were spleen (1), thymus (9), prostate (24), testis (4), ovary (2), small intestine (1), colon (1), and PBL (350). None of the tissues originated from the same donor.

EXAMPLE 5

Reverse Transcription-PCR

RT-PCR was performed using the Gene-Amp RNA-PCR kit (Perkin-Elmer) containing MULV RT according to the manufacturer's instructions. RT was performed with either random hexamer or oligo d(T) priming. In all cases, 1 μl of total RNA (250 ng/gl) and 20 ng of each second step PCR primer was used (20 ng/μl). For the second step PCR, additional MgCl2 was omitted from the reaction mix since the primers worked best under low salt conditions. RT and amplification steps were performed in a Hybaid thermocycler (Labnet). PCR conditions were as follows: 1 cycle at 95° C. for 2.5 min; 40 cycles at 95° C. for 1 min, annealing temperature for 1 min, 72° C. for 30 sec; and a final cycle at 72° C. for 5 min. Annealing temperatures are given in Table 1.

TABLE 1

| RT-PCR Primers and Conditions* | | |
|---|---|---|
| NAME | SEQUENCE | |
| B27F2 | TGCCCTCCCTCCCCATCCCTC | (SEQ ID NO: 4) |
| B27R2 | ACGGGGGTCTCTGTGCATTCTGA | (SEQ ID NO: 5) |
| B27F3 | AGGCCGCCTATGTTTTTCTCAG | (SEQ ID NO: 2) |
| B27R3 | GCTCCTTTTCTGCTCTGCTCTTCT | (SEQ ID NO: 3) |
| B27F4 | CAACCCCCTCCCCGCACCC | (SEQ ID NO: 6) |
| B27R4 | CTGATTGTGTGCTGCAGTGTGCTG | (SEQ ID NO: 7) |
| GRAIL-R | CACTGCTCCATTGTCCTTGTCCC | (SEQ ID NO: 8) |
| PRIMER PAIR | ANNEALING TEMP | PRODUCT SIZE |
| F2/R2 | 62 | 316 |
| F2/R3 | 62 | 251 |
| F2/R4 | 60 | 80 |
| F3/R2 | 54 | 352 |
| F3/R3 | 56 | 287 |
| F3/R4 | 54 | 116 |
| F4/R2 | 58 | 286 |

TABLE 1-continued

| RT-PCR Primers and Conditions* | | |
|---|---|---|
| F4/R3 | 60 | 221 |
| F4/R4 | 58 | 50 |
| F2/GRAIL-R | 61 | 409 |
| F3/GRAIL-R | 56 | 445 |
| F4/GRAIL-R | 58 | 379 |

*All primers are shown in the 5'-3' orientation

EXAMPLE 6

Purification of RT-PCR Products

Purification of RT-PCR products was performed using the Qiaquick Spin PCR Purification kit (Qiagen) according to the manufacturer's instructions. Since only single bands were obtained, the entire PCR reaction was diluted and loaded onto the column. No size selection was performed.

EXAMPLE 7

Sequencing

For double stranded genomic sequencing, the Sanger dideoxy sequencing technique was performed using the Sequenase and Sequenase II kits (US Biochem) according to the manufacturer's instructions with pyrophosphatase added to the enzyme dilution buffer to produce uniform band intensity. The only modifications made were in the dilution and incubation times of the labeling mix and the amount of template. In addition, 6% Long Ranger Gel Solution (AT Biochem) rather than either 5% (as suggested by the manufacturer) or 8% PAGE gave the best results.

Double stranded sequencing was initiated on the 6.5 kb EcoRI inserts from the Bluescript multiple cloning site by T7 and T3 primers (Stratagene). All 3 inserts were subcloned in the same orientation, such that T7 primed on the 5' end of the B27 gene and T3 primed on the 3' end of the fragment. After the first sequences were obtained, oligonucleotide primers were designed to obtain additional sequence information.

Sequencing of RT-PCR products was performed using the Sequenase-PCR kit (US Biochem) according to the manufacturer's instructions. Sequencing gels were 8% PAGE, prepared and run in glycerol tolerant (Taurine based) buffer. Dilutions of labeling mixes were as described for genomic sequencing, but in all cases, 50 ng of purified PCR product was used with 10 ng of primer.

EXAMPLE 8

Sequence Analysis

GCG (Genetics Computer Group Version 7 (1991) programs) GELSTART, GELENTER, GELASSEMBLE, LINEUP, and PRETTY were used to create the initial sequences and later to align each of the sequences obtained. For the sequence data, all overlaps and alignments were performed manually rather than relying on the computer to perform these functions. For analysis of nucleotide (nt) and peptide sequence homologies and open reading frames (ORFs), several programs were used for searches performed on the parallel processors of the NCBI.NLM.NIH computers via Internet [available via a "help" message to "blast@ncbi.nlm.nih.gov"]. For nt searches, the program BLASTN (Altschul et al. *J. Mol Biol* 215:403–410 (1990)) was used on the nonredundant nt databases. For peptide searches, the nt sequence was analyzed by first using the GCG program MAP to find all open reading frames beginning with a Met initiation codon and then submitting these ORF sequences to the BLASTP program of the NCBI computer for comparison to the nonredundant peptide databases. The nt sequence was also submitted directly to the NCBI program BLASTX which translates the sequence in all six translation frames, irrespective of whether Met is present at the initiation site, and then automatically searches the nonredundant peptide databases. These programs generate results which list the highest scoring homologies found, their significance values, the reading frames and locations within the sequences which match, the percent similarity and percent identity, as well as which strand (forward or reverse) has the homology. For peptide searches, the filters SEG+ XNU were always used. Additionally, to analyze potential coding regions in the newly derived sequence, the program GRAIL available through ORNL.GOV was used.

A number of other GCG programs were used repeatedly for manipulation of sequence data and for finding important regions in the sequence. Those most used were the programs FIND, which allows one to locate a region of short homology in a long sequence, and MAP which allows one to find virtually all restriction sites within a sequence of interest.

Sequence Identification of a Single Polymorphism in the HLA-B27 3' Flanking Region Correlating with Resistance to Ankylosing Spondylitis and Reiter's Syndrome

EXAMPLE 9

TaqI RFLP

The disease status of the individuals studied in this example (all of whom were B27+ ) were as follows: 32 unrelated normal, 38 AS, and 20 Reiter's syndrome (RS) probands. Blood relatives (n=128) representing the families of 31 of these B27+ probands were also recruited and 110 of these blood relatives were also tested. Individuals were typed for HLA-A, B, C and their genomic DNA digested with TaqI and analyzed using the B locus specific probe, EI7, in the standard Southern technique. Each group of probands was ethnically heterogeneous as shown in Table 2; however, a 2.5 kb TaqI fragment has been found in every ethnic group studied to date and therefore the data were pooled. Table 3 shows that the 2.5 kb RFLP is not evenly distributed among the groups but has a much higher frequency in the normal B27+ population (Yates corr. $X^2=6.283$, p=0.0122).

TABLE 2

Ethnicity of B27+ probands assessed for TaqI RFLP

| | DISEASE CATEGORY | | |
|---|---|---|---|
| | Normal | AS | RS |
| ETHNIC GROUP | | | |
| Caucasian | 30 | 23 | 11 |
| Black | 1 | 1 | — |
| Hispanic | 1 | 4 | 3 |
| Asian | — | 10 | 5 |
| | 32 | 38 | 20 |

TABLE 3

Presence of 2.5 kb TaqI RFLP in patients and normals

| | 2.5 kb+ | 2.5 kb− | Total |
|---|---|---|---|
| Normal | 11 | 21 | 32 |
| Patient | 6 | 52 | 58 |
| Total | 17 | 73 | 90 |

Yates corr. $\chi^2 = 6.283$
p = 0.0122

This is true even when the analysis is limited to Caucasians, although the significance is borderline at p=0.05. It has been found that the odds ratio for an individual with the 2.5 kb TaqI RFLP to be disease free is 4.54 times higher than for individuals without the 2.5 kb TaqI site (95% confidence interval=1.48–13.87). DNA sequencing results indicate that the actual size of this fragment is 2.425 kb.

Since family studies confirmed that the B27 TaqI RFLP was inherited as a haplotypic marker (Ness D.B. and Grumet F.C. *Hum Immunol* 18:65–73 (1987)), it was of interest to know what relationship the RFLP might have to the already described B27 IEF variants. Thirteen DNA samples that were previously characterized for IEF subtype were tested with TaqI in our laboratory. Cell lines from 10 individuals who had been characterized for their TaqI RFLP were characterized by IEF. No correlation was observed between the subtypes and the TaqI RFLP, except that the 8.0 kb TaqI RFLP was never associated with the common B*2705 variant.

EXAMPLE 10

Sequence

The B27 gene and the associated polymorphic site are contained on an EcoRI fragment and an equivalent EcoRI DNA fragment carrying an affected B27 gene causes transgenic rats to display a disease phenotype. We compared sequences of the B27+ EcoRI fragments from five different individuals including the one from whom the transgene originated, and two of whom we knew differed for the TaqI site on their B27 haplotype by family studies or restriction mapping.

DNA sequencing was performed initially on the clearly distinctive B27+ EcoRI fragments from one unaffected (B27HS) and one affected (B27GV) individual differing for the TaqI RFLP, and therefore derived from different B27 haplotypes. Differences were noted between these two genes and the original CD2.6 sequence described in Weiss et al. Immunobiol 170:367–380 (1985). In order to verify these differences, the "healthy" B27WE subclone from CD2.6 was sequenced over the regions of disparity as well as in the 5' and 3' regions not previously sequenced. Likewise, the affected B27TA clone (pE.1-B27), which was used as the transgene in Hammer et al. Cell 63:1099–1112, 1990, was sequenced in its entirety. Finally, another B27 unaffected clone (B27DL) was sequenced over regions of disparity as well. Thus, a total of two known unaffected, two known affected, and one "healthy" B27 gene along with the corresponding flanking regions were sequenced in all or part. Four of these five were confirmed to carry the B*2705 subtype. Since B27DL was only sequenced over regions of variation, it was not sequenced in exons 2 or 3 to confirm its subtype.

The results of the genomic sequencing obtained in the course of this work were aligned with all known B27 genomic sequences. The consensus sequence is provided in SEQ ID NO:1. Table 4 gives the landmark features of the known B27 sequence and the cDNA numbering for comparison. Sequences obtained from cDNA were not included because they are not useful for comparison of non-coding regions. The genomic sequences for B*2703, B27K, B27W, and CD2.6 have all been previously published (Weiss et al. Immunobiol 170:367–380 (1985), Seemann et al. EMBO J 5:547–552 (1986), and Choo et al. *Hum Immunol* 21:209–219 (1988)). Varying amounts of flanking sequence are included in these published sequences, except that no 3' flanking sequences have been described beyond nucleotide 4457 of SEQ ID NO:1. The five sequences which were sequenced in the course of the present invention are denoted B27TA, B27GV, B27DL, B27HS, and B27WE.

TABLE 4

Conversion table and locations of known B27 sequence elements in EcoRI sequence

| EcoRI position | B27 region | Residue |
| --- | --- | --- |
| 480–492 | CRE/Enhancer A | |
| 501–515 | IRS | |
| 602–606 | CCAAT | |
| 628–633 | TATA | |
| 679–751 | X1 | |
| 752–880 | I1 | |
| 881–1150 | X2 | 1–90 |
| 1151–1396 | I2 | |
| 1397–1672 | X3 | 91–182 |
| 1673–2247 | I3 | |
| 2222–2329 | Alu (C' strand) | |
| 2248–2523 | X4 | 183–274 |
| 2524–2616 | I4 | |
| 2617–2733 | X5 | 275–313 |
| 2734–3174 | I5 | |
| 2816–2889 | Alu - Sx (C' strand) | |
| 3175–3207 | X6 | 314–324 |
| 3208–3313 | I6 | |
| 3285–3556 | E17 probe | |
| 3314–3361 | X7 | 325–338 (or 340?) |
| 3362–3543 | I7 | |
| 3544–3545 | X8? | 341? |
| 3546–3967 | 3'UT | |
| 3944–3949 | polyA signal | |
| 3968–6653 | 3' Flanking | |

EXAMPLE 11

Comparison to Published B27 Genomic Sequences

Sequencing of B27HS and B27GV revealed regions of differences when compared to the original B27 genomic sequence of CD2.6. To elucidate the importance of these discrepancies, an EcoRI subclone of CD2.6, which was termed B27WE, was obtained and sequenced. The sequence of the B27WE subclone differs from that originally published for its parent clone CD2.6. Many of the initially observed disparities between B27HS or B27GV and this original CD2.6 gene disappeared upon sequencing the subclone and the sequences were found to be nearly identical. Inclusion and final alignment of the other published sequences (B27W, B27K, and B*2703) introduced additional areas of discrepancy not found in any of our five sequences.

Aside from the substitutions which distinguish the B*2702 and B*2703 subtypes and which have been previously described (Seemann et al. *EMBO J* 5:547–552 (1986), and Choo et al. *Hum Immunol* 21:209–219 (1988)), the sequences of B27K (B*2702) and B27W (B*2705) are identical to each other but differ at 36 positions from all other sequences, including the four other confirmed B*2705 genes which were sequenced. The B*2703 sequence also varies uniquely at 11 positions in noncoding regions, 9 of which are in introns. For the B27K and B27W sequences, 6 changes are in intron 1 (I1), including an apparent deletion (−1 frameshift) at position 815 of SEQ ID NO:1 and a compensating insertion (+1 frameshift) at position 822 of SEQ ID NO:1. There are also 10 differences in I2 with one at position 1273 eliminating a TaqI site and a 2 nt insertion not found in any of the other genes at positions 1386/7 of SEQ ID NO:1. In I3, aside from the gap noted in the original report, 7 nucleotides differ, all but one of which are deletions. There are two differences in I4, three in I5, one in I7, and five in the 3∝ UT. No sequence information is available for the 3∝ flanking region.

B*2703 also has 11 unique differences from the consensus sequence in noncoding regions with two changes in I1, four in I2, one in I5 and two in I7. An additional two changes were noted in the 3' flanking sequence at positions 3980 and 4184 of SEQ ID NO:1.

EXAMPLES 12

Characteristics of EcoRI Insert

The data we obtained by sequencing the five independently derived B27+ EcoRI fragments indicate that the EcoRI insert is 6551 bp long beginning with the initial G (GAATTC) at the 5' site and ending with the final C at the 3' site. The discrepancy in length of the EcoRI fragment shown in SEQ ID NO:1 (6553 bp) is due to the 2 nt insertion in the B27W and B27K sequences at 1386/7 mentioned above. There are 678 nt 5' of the first base of the leader sequence and 2586 nt 3' of the last base of the 3' UT, most of which (2250 nt) were previously unknown. There are six potentially polymorphic TaqI sites at nucleotides 986, 1270, 2070, 4494, 5310 and 5923 of SEQ ID NO:1. It has been found that the TaqI polymorphic site that is indicative of a genetic predisposition to seronegative spondyloarthropathies lies in the 3' flanking region and is found at position 4494, just 527 nt 3' from the end of the 3' UT region of the B27 gene.

EXAMPLE 13

Coding Region

First, it was determined whether coding region differences existed between B27+ patients and normals. Sequencing primers for exons were designed from the published B27 sequences and coding regions compared to determine whether the polymorphic TaqI site at about nucleotide 4495 of SEQ ID NO:1 was a marker for structurally distinct B27 genes. Comparison of the sequences of the normal B27HS and healthy B27WE to those of patients B27GV and B27TA reveal that there are no differences in the B27 coding regions of these clearly distinguishable B27 haplotypes. The results with unaffected and affected individuals carrying clearly different B27 haplotypes accord with the previous reports of Coppin and McDevitt *J Immunol* 137:2168–2172 (1986), Weiss et al. *Br J Rheumatol* 27(Suppl II) :12–18 (1988), and Higgins et al. *Ann Rheum Dis* 51:855–862 (1992) in which B27 genes from random healthy and AS probands ascertained only by their historic and current disease status were sequenced and no differences in the B27 coding sequences were found.

The results also indicate that no microheterogeneity exists in B*2705 structural genes which confers susceptibility/resistance to disease. The results also reveal that the B27 structural gene as presently defined and without modification cannot explain the association between B27 and AS nor can it explain why most B27+ individuals do not get disease. Each B27 structural gene, whether from a normal or affected individual would be predicted to yield the same protein.

EXAMPLE 14

5' Flanking, Introns, and 3' Untranslated Regions

Next, 5' flanking, introns, and 3' UT regions were sequenced to determine if differences within the B27 regulatory regions or known transcripts might explain the association with disease. In comparing four of the B27 genes sequenced, no differences were found between patients B27GV and B27TA and healthy individuals 227HS and B27WE in the 678 nucleotides 5' of the leader sequence. The healthy B27DL was not sequenced in this region because there were no regions of variation with which to compare it. The absence of any 5' flanking variation in the genes we sequenced suggests that differences in promoters or upstream regulatory elements is not the basis for differential disease susceptibility among B27+ individuals unless these regions reside further upstream. However, the presence of only 678 nt of 5' flanking sequence on the EcoRI fragment inserted into the rats is sufficient for expression of the disease phenotype (see, e.g., Hammer et al. Cell 63:1099-1112, 1990) suggesting that this region alone is not responsible for the differential susceptibility.

Comparison of the non-coding sequences for polymorphism in possible regulatory elements resulted in only a single difference in an intron of one of the genes that was sequenced. The one sequence alteration observed was in I1 at 809 in B27TA where it shares a deletion of 1 nt with B*2703. It is unlikely that this difference is relevant to disease susceptibility, however, since 3*2703 has only been found in a few normals to date, whereas B27TA is from an AS patient. In addition, B27GV is also from an AS patient but does not have this deletion. These data suggest that differential disease susceptibility cannot be ascribed to polymorphic enhancers present in introns, nor to differential mRNA stability controlled by a polymorphic 3' UT region.

EXAMPLE 15

3' Flanking Region

A B27+ transgenic rat was produced using as the transgene the same clone (pE.1-B27/B27TA) that was sequenced in accordance with the present invention, but which has been shown not to be different in the coding regions from unaffected B27 genes. Importantly, the B27 transgene contains nearly as much 3' flanking genomic sequence (2.59 kb) as is accounted for by the B27 gene itself (3.29 kb). In the EcoRI fragment from individual B27TA that was sequenced, only eight point substitutions were identified: the single deletion in I1 discussed above and seven others, all in the 3' flanking region (Table 5). Six of them are uniquely distributed at positions 4023 (GV), 4291 (WE), 4586 (TA), and 5029, 5031, 5052 (GV) of SEQ ID NO:1. Since six differences in the 3' flanking region were uniquely distributed among the five sequences, any one of these cannot account for the differences in disease status.

TABLE 5

| | HLA-B27 3'-flanking polymorphisms | | | | | | | | |
|---|---|---|---|---|---|---|---|---|---|
| | 3980 | 4023 | 4184 | 4291 | 4495* | 4586 | 5029 | 5031 | 5052 |
| 3'FL: | 13 | 56 | 217 | 324 | 528 | 619 | 1062 | 1064 | 1085 |
| B*2703 | G | — | . | ND | ND | ND | ND | ND | ND |
| B*2705 TA | — | — | — | — | — | C | — | — | — |
| B*2705 GV | — | T | — | — | — | — | A | . | A |
| B*2705 WE | — | — | — | C | — | — | — | — | — |
| B*27 DL | — | — | — | — | C | — | — | — | — |
| B*2705 HS | — | — | — | — | C | — | — | — | — |
| CONSENSUS | C | G | C | T | A | T | T | G | C |

*4495 = TaqI polymorphic site

The seventh point substitution is a conserved dimorphism found at position 4495 SEQ ID NO:1 which also accounts for the presence or absence of the TaqI polymorphism. Notably, the diseased B27TA differs from the unaffected B27HS at only three positions, one in I1 (809) and the other two in close proximity to one another in the 3' flanking region (4495, 4586). Thus, in B27GV and B27TA, derived from patients, the sequence is "TAGA" (nucleotides 4494-4497 of SEQ ID NO:1) while in B27HS and B27DL, derived from verified normal individuals, it is "TCGA." It is the only difference among the B27 genes we studied which is consistent with disease status. Thus far, the most common sequence found in B27+ individuals is TAGA with an alteration to TCGA in 34% of B27+ normal individuals. This change appears to be protective, making it 4.5-fold more likely that individuals with the -TCGA- variant sequence will not get disease.

EXAMPLE 16

Open Reading Frames (ORFs)

In order to determine whether the newly obtained 3' flanking sequence contained possible protein coding regions or other areas of interest, computer searches using the entire EcoRI sequence were performed as described in Materials and Methods. Using the GCG program "MAP", 22 ORFs more than 59 aa long and 11 longer than 100 aa were identified with Met at the initiation site as shown in Table 6.

TABLE 6

Open reading frames beginning with Met in EcoRI insert.

| Name | Length | Sequence position | B27 region |
|---|---|---|---|
| Forward ORFs | | | |
| B2 | 77+ | 2–232 | 5' flanking |
| B524 | 70 | 524–733 | 5' - X1 |
| A679 | 159 | 679–1155 | X1, X2 |
| A1417 | 115 | 1417–1761 | X3 |
| B3338 | 102 | 3338–3643 | X7 - 3'UT |
| C4971 | 70 | 4971–5180 | 3' flanking |
| C5757 | 63 | 5757–5945 | 3' flanking |
| A6376 | 59+ | 6376–6553+? | 3' flanking |
| Reverse ORFs | | | |
| F6027 | 79 | 6027–5791 | 3' flanking |
| E5474 | 123 | 5474–5106 | 3' flanking |
| D5401 | 73 | 5401–5183 | 3' flanking |
| F5211 | 61 | 5211–5029 | 3' flanking |
| F4674 | 87 | 4674–4411 | 3' through TaqI |
| E4547 | 123 | 4547–4179 | 3' through TaqI |
| D3976 | 122 | 3976–3611 | 3' flanking - 3'UT |
| F3624 | 124 | 3624–3253 | 3'UT - 16 |
| E3161 | 143 | 3161–2733 | I5 |
| E2489 | 81 | 2489–2247 | 14 - X4 |
| F2244 | 60 | 2244–2065 | 13 |
| F1191 | 174 | 1191–670 | 12 - X1 |
| E947 | 113 | 947–609 | X2 - 5' flanking |
| D565 | 141 | 565–143 | 5' flanking |

Forward strand = B27 sense strand
Forward strand frames: A–C
Reverse strand frames: D–F The minimum size of 59 aa was selected in order to include the ORF at the 3'end of the insert whose actual length is unknown due to the introduction of the EcoRI cloning site.

Eight of the ORFs are on the forward (B27 sense) strand. Of these, three are more than 100 aa long encoding B27 exons 1–3 (X1–3) as expected. Exons 4–6 were not identified by the computer as ORFs even though X4 is 92 aa in length. This is due to the absence of a Met in this ORF which eliminates it from consideration when the program MAP is used. Thus this algorithm significantly underestimates the true number of ORFs. The five ORFs outside of the B27 transcribed region are all less than 100 aa in length and none has significant homology with any known proteins.

On the complementary (reverse) strand there are 14 ORFs; eight are more than 100 aa long. Of the 14, ten show no significant homology to known proteins. The remaining four are of particular interest, however.

Of most interest was a 123 aa ORF (E4547) which reads through the variable TaqI site at nucleotide 4495 of SEQ ID NO:1. In this reading frame the alteration of A to C at the TaqI site results in the nonconservative substitution of a putative Leu (CTA) at this position in the common B27 haplotype with an Arg (CGA) in the B27 haplotypes carrying the 2.5 kb TaqI RFLP without altering the length of the ORF. When BLASTX was run on the Transcription Factor Dataset (TFD), 36 homologies with p<0.05 were found, the most significant being with the engrailed (p=1.1 X 10–4), bicoid, Oct-1, Oct-2 and 10 other factors. In addition, results using the GRAIL algorithm to identify likely coding regions in an unknown sequence suggest that at least a portion of this region (4248–4089) has the potential to be a protein coding region as well. The mean score for this region is 0.73, with most noncoding regions equal to 0 and most exons approaching 1. It is the only potential coding region besides those belonging to B27 which was identified for the entire sequence. Searches of the nt and peptide databases showed possible homologies to human laminin B2 chain (67i identity), human apolipoprotein (67% identity), and the R. meliloti probable sigma (54) modulation protein (SwissProt P17625). In each case, the region of homology crosses the TaqI polymorphic site at position 4495 of SEQ ID NO:1.

Also of interest was the 123 aa ORF E5474 set forth in Table 6. Searches of the nt and EST databases revealed that this ORF contains a region of highly significant homology (1.4e-10) to a C. elegans EST (GenBank M79621) with 71% identity over a 100 nt length (5265–5166 in SEQ ID NO:1). Similarly, there is highly significant homology (p=5.7e-5) with X1 of human hepatic lipase (GenBank M35425). In this same region on the forward strand (5168–5292), there is 60% identity over 125 nt length with a human liver tissue putatively transcribed partial sequence (GenBank Z19990). It is not known whether these two latter sequences derive from the same protein. However, no ORF of substantial length (with or without a Met initiation codon) on the forward strand was detected in this region.

A third ORF (E3161, 143 aa) is antisense to all but 13 nt of the 441 nt long I5 of B27, ending with a 1 nt overlap into X5. Its highest scoring homology is with the M. leprae secD gene to which it has 45% similarity. It also has homologies with rat and human collagen, the human CR1 gene, and the outer capsid proteins of human rotavirus A, but the p values suggest these may not be significant. Similarly, a fourth 81 aa ORF (E2489) is antisense to X4 beginning 34 nt downstream from the end of the exon and ending 1 nt 5' of its start. It shows no significant homology to any known proteins.

In order to be as inclusive as possible, searches were also performed of the entire 3' flanking sequence using the BLASTX program with filters on the nonredundant peptide and EST databases. This program has the advantage of comparing all ORFs regardless of their initiation codons. More than 300 homologies were found with 44 of them having p values ranging from 0.044–1.7e-8. The homologous sequences could generally be classified as extracellular matrix (ECM) proteins and were often proline rich. They included extensins, amelogenin, and mucins. Additionally, they included regulatory proteins such as DNA-directed RNA polymerase, RNA replicase polyprotein, and Herpes virus EBNA-2 transactivator. All of the ECM and regulatory homologies were found with comparisons to the strand complementary to B27.

Having identified the ORFs, it was of interest to know whether any of the seven point substitutions found in the 3' flanking region of the genes that were sequenced lay in the ORFs. Surprisingly, all but one did and all of them resulted in amino acid changes in the putative peptides which would be encoded by these ORFs. Of the two 3'-flanking substitutions seen in B*2703, one lies in one of the ORFs identified, the other does not. The results are shown in Table 7.

TABLE 7

Putative amino acid changes due to point substitutions in HLA-B27 3'-flanking region

|  | 3980 | 4023 | 4184 | 4291* | 4495 | 4586 | 5029 | 5031 | 5052 |
|---|---|---|---|---|---|---|---|---|---|
| B*2703 | G | — | . | ND | ND | ND | ND | ND | ND |
| B*2073 | G | — | . | ND | ND | ND | ND | ND | ND |
| B*2705 TA | — | — | — | — | — | C | — | — | — |
| B*2705 GV | — | T | — | — | — | — | A | . | A |
| B*2705 WE | — | — | — | C | — | — | — | — | — |
| B*27 DL | — | — | — | — | C | — | — | — | — |
| B*2705 HS | — | — | — | — | C | — | — | — | — |
| CONSENSUS | C | G | C | T | A | T | T | G | C |
| ORF | None | 4547 | | 4674 | | 4971 / 5211 | | | |
| FRAME |  | E | | F | | C | F | | |
| LENGTH |  | 123 | | 87 | | 70 | 61 | | |
| CHANGE |  | D>M E>G L>R | | Y>C | | M>K A>Q Q>K P>H G>W | | | |

Of greater interest is the fact that 3 of 7 (3/7) substitutions, including that generating the TaqI polymorphic site at nucleotide 4495 of SEQ ID NO:1, lie in the same ORF (E4547).

EXAMPLE 17

Polymorphic TaqI Site Lies in Transcriptionally Active Genome Region

Having determined in Examples 9 to 16 above that only a single difference exists in the 6551 bp EcoRI genomic insert which correlates with disease and that this is in a putative ORF, RNA studies were initiated to determine whether this ORF might be in a transcriptionally active region.

Three sets of primers internal to the putative ORF and amplifying over the polymorphic TaqI site were synthesized (Table 1: F3/R3; F2/R2; and F4/R4) and tested in various combinations on B27HS DNA to determine appropriate PCR conditions. In addition, the primer pairs GRAIL-R/F3 (Table 1; SEQ ID NO:8/SEQ ID NO:2) and GRAIL-R/F2 (SEQ ID NO:8/SEQ ID NO:4) were also employed in the experiment described herein. When the conditions were satisfactorily determined, RT-PCR studies were instituted as described in Materials and Methods. Initially, RT-PCR was performed using random hexamer priming for the RT step since it was unknown whether any RNA present would be polyadenylated. Positive results were obtained using various combinations of the primer pairs on RNA from PBLs of a single individual. In all cases RNA-derived products of the size expected from the corresponding genomic sequence were obtained indicating the absence of introns in the amplified regions, including nucleotides 4112–4556 of SEQ ID NO:1 (product of primer pair GRAIL-R/F3).

However, when the primer pair GRAIL-R/F4 was used, the expected 379 base pair amplification was not detected in all cases, but instead amplification products of only about 200 bp were detected in some individuals, which indicates the presence of an alternatively spliced variant.

To determine whether both PBL and LCL had the transcript containing the location of the TaqI site and whether it was polyadenylated, further RT-PCR studies were performed using the B27ORFF3 and B27ORFR3 (F3,R3) primers because they gave a 287 bp product. Each of the RNA preps from 3 PBL and 3 LCL were tested using oligo d(T) priming in the initial RT step. For comparison, the same RNAs were primed with random hexamers as a positive control for the RT step and cyclophilin was used as a positive control for the subsequent PCR step. The results confirm that the transcript is polyadenylated and is present in both PBL and LCL. Of great interest, however, was the single B27 negative individual included. This individual clearly has intact polyA+ RNA as indicated by a positive result with cyclophilin. However, no product was seen with the F3/R3 primers regardless of whether random hexamers or oligo d(T) were used in the RT step, suggesting that one or both of these primers cannot bind or, alternatively, no transcript is produced from this region.

To confirm this result, total RNAs were isolated from an additional 4 B27 negative individuals, DNase treated, and tested in similar fashion. Furthermore, it was important to confirm that the PCR products were not due to residual DNA contamination. For this purpose, the 4 new B27 negative RNAs together with one of the previously positive B27+ RNAs were run in parallel under identical conditions using oligo d(T) for RT and either F3/R3 or cyclophilin primers for PCR. However, for each sample, one tube had water rather than MuLV RT added in the RT step. All samples otherwise underwent identical handling. The results show unequivocally that the RT-PCR product using the F3/R3 primers can be obtained in the B27+ individual and is not the result of residual DNA contamination. However, no F3/R3 product is detectable in any of the 4 additional B27 negative individuals tested, although the cyclophilin controls gave the expected product. Thus, all five (5/5) B27+ individuals display an RT-PCR product with F3/R3 primers while none of the five (0/5) B27- individuals display such a product. Further, 4 of the B27 negative individuals were chosen because they had one or more B locus alleles in the B27 crossreactive group (CREG), suggesting that even highly related genes are either polymorphic in this region or transcriptionally inactive.

The results indicated that: (1) only single PCR bands were obtained under optimal conditions with any of the ORF primer pairs, (2) the PCR bands were always of the expected size, and (3) nested PCR also gave the expected fragment size. Nonetheless, it was important to sequence the PCR products to confirm that they corresponded to RNA derived from the expected genomic region. For this purpose both the random hexamer and oligo d(T) primed PCR products obtained from individuals HS and JR were purified. Sequence data on the purified oligo d(T) primed products (amplified in the PCR step with primers R3 SEQ ID NO:3 and F3 SEQ ID NO:2) was identical to the genomic sequence over 190 nt of readable sequence beginning 3 nt from the 3' end of the sequencing primer (F3) indicating that the PCR products are in fact derived from the region of interest.

Finally, it was important to determine whether the transcript could be detected on a Northern blot and what its approximate size might be. For this purpose, a Northern containing total RNA from 7 B27+ LCL as well as a commercial Multiple Tissue Northern blot from individuals of unknown HLA type were probed using the previously mentioned purified PCR product from the random hexamer priming and R3/F3 amplification of HS. The results indicate that for the total RNA blot, two strong bands (2.5 kb, 1.9 kb) are evident. While formally possible, it is unlikely that the 1.9 kb band represents 18S RNA since the washing conditions were quite stringent. In any case, the 2.5 kb fragment is unrelated to rRNA. The results of a 19 hr exposure on the Multiple Tissue Northern indicate that two transcripts are evident, one at 5.8 kb and another at 2.35 kb, with additional transcripts of 2.0 kb and 1.1 kb seen in mRNA from small intestine. The 2.35 kb transcript is similar in size and likely identical to the 2.5 kb transcript seen in the lymphoblastoid cell line (LCL). Of interest, the 5.8 kb transcript is reduced in thymus and ovary while the 2.35 kb transcript is nearly absent in these two tissues as well as PBLs. The β-actin control clearly indicates that this is not due to quantitative differences in the amounts of polyA+ RNA loaded per lane. An additional transcript of 1.1 kb is seen in small intestine.

The most significant results obtained thus far are those derived from RNA studies of the putative ORF which lies only 145 nt downstream of the 3' end of the B27 gene at a maximum. Results from RT-PCR experiments using RNA derived from B27+ individuals clearly show that the genomic region through the polymorphic site at 4495 is transcriptionally active and is minimally 445 bases long without interruption, (i.e., nucleotides 4112–4556 of SEQ ID NO:1 produced with primer pair GRAIL-R/F3). Northern analysis suggests that multiple transcripts are present differing in size (5.8, 2.35, 2.0, 1.1 kb) and tissue distribution. The transcripts are absent or in low abundance in thymus and ovary but the 5.8 and 2.35 kb transcripts appear to be well expressed in spleen, prostate, testis, small intestine, and colon. In addition, the 1.1 kb transcript is found only in the small intestine sample. A 2.5 and 1.9 kb transcript appear to be well expressed in B27+ LCL. The absence of the 5.8 kb transcript on the total RNA Northern may be an artifact of having -transferred in 20X SSC which tends to reduce transfer of species greater than 4 kb. Pooled PBLs show differential abundance of the transcripts with good expression of the 5.8 kb transcript but absence/low abundance of the smaller species. Given the male predominance in AS and RS patients, it is of interest that the male tissues of prostate and testis show relatively abundant expression of the transcripts while the female ovarian tissue has low expression. It is also of interest that an additional transcript is found in RNA from small intestine given the increased susceptibility to AS of B27+ inflammatory bowel disease patients.

It is unclear at present whether these transcripts are present in B27 negative individuals since RT-PCR results using the F3/R3 primer pair were consistently negative in the 5 B27 negative individuals tested. Whether this is due to polymorphism at one or both priming sites or to absence of the mRNA is not known.

However, the fact that transcripts are observed in the Multiple Tissue Northern blot composed of pools of some tissues which are unlikely to be uniformly B27+ suggests that the former possibility is more likely. It is also unknown at present which strand is transcriptionally active because both forward and reverse primers were used for RT-PCR studies and double stranded PCR products were used to probe Northerns. The internal primers used in the RT-PCR experiments were designed as if the transcriptionally active strand were complementary to B27. If this is correct, the presence of the RT-PCR product only in B27+ individuals would suggest either the presence of a gene closely linked to B27 which is coordinately regulated and transcribed only in B27+ individuals or a polymorphism in this region not seen in B27 haplotypes.

Investigation of the putative upstream sequence of the transcript (B27 complementary orientation) shows that the ORF extends 61 bases 5' of the TaqI polymorphic site to the 5' end of the F3 primer before a potential stop codon is encountered. There is a complete absence of canonical TATA sites on this strand. Although the B27 gene itself has a noncanonical TATA box (TCTAAA) , no such sites are observed upstream of the F3/R3 transcription region (nucleotides 4270–4556 SEQ ID NO:1). In fact, the transcript would be expected to be from an internal (exon?) coding sequence since it begins (at minimum) with an Arg three codons prior to the Met originally identifying the ORF. The nearest potential CCAAT box can be found at 4691 which is 135 bases upstream of the F3 primer, the 5' demarcation border of the transcript in the current studies if the transcript is encoded by this strand. Additionally, there is no polyA addition signal on this strand between the transcriptionally active region and the EcoRI cloning insertion site 4.2 kb downstream suggesting that if the smaller transcripts (2.5–1.1 kb) derive from this strand, they are antisense to B27 and spliced.

Transcripts derived from this strand are potentially the most interesting with respect to disease susceptibility since in 2 of 3 reading frames the transcript would be polymorphic [CTA(Leu)/CGA(Arg) and TAC(Tyr)/GAC(Asp)] and might suggest a basis for differential susceptibility of B27 haplotypes. However, it is only in the reading frame described (E4547) that no stop codon is encountered in the transcriptionally active region. Since the RT-PCR studies performed here on patients and normals do not support differential transcript lengths in this region, it is likely that only this single reading frame would be the one transcribed.

Alternatively, the B27+ strand could also be the active strand. If this were true, the fact that the transcriptionally active region minimally extends to within 145 bases of the end of the 3' UT of B27 would be consistent with either an extraordinarily tightly linked gene to B27 or with an alternative 3' splice site for the B27 mRNA which has been heretofore unrecognized. Since there are multiple stop codons in the transcript region in all three forward (B27 sense) frames, this region is unlikely to code for a new gene. However, it is interesting that there is an additional polyA addition signal at nucleotide 4624 of SEQ ID NO:1, just 67 bases downstream of the F3 primer (on the B27 strand) and only 656 bases from the currently recognized 3'UT end of the B27 gene. Thus it is possible that the B27 gene is being alternatively spliced in a manner including the polymorphic region through 4495, although it is difficult to reconcile the transcript sizes seen on Northerns with this possibility. The transcripts appear to be much smaller or larger than would be expected and would suggest more than just the simple substitution of an alternate 3'UT region.

Furthermore, it would be more difficult to envision a mechanism for differential disease susceptibility since there is no polymorphism associated with the RT-PCR transcript in 2 of 3 reading frames [GTA(Val)/GTC(Val) or AGA(Arg) /CGA(Arg)] on this strand and the third reading frame introduces/removes another stop codon [TAG(Stop)/TCG (Ser)]. Although the currently defined 3'UT of B27 also has stop codons in every reading frame, and a "premature" stop codon would be of great interest, the lack of polymorphism in the F3/R3 transcript size (i.e., lack of a truncated transcript) suggests that this potential polymorphism could be irrelevant.

EXAMPLE 18

Seronegative Spondyloarthropathy Genetic Predisposition Assay

DNA or RNA from a subject suspected of having a seronegative spondyloarthropathy is extracted and quantitated by standard procedures from 20cc of peripheral blood obtained by venipuncture from test subjects. RNA (total or mRNA) may be subjected to an additional DNase treatment (3 u/μg) to remove any contaminating DNase. cDNA is then prepared by using an oligo dT primer and MuLV reverse transcriptase. After quantitation of the cDNA, PCR amplification using combinations of the primer paris (e.g., F3/R3) is performed with conditions appropriate to each primer pair in a 100 μl final volume. The product (e.g., F3/R3 gives a 287 bp product on cDNA from B27 positive individuals) is then run on a size fractionating gel with appropriate marker lanes and visualized with ethiduim bromide to assure that amplification has occurred. Once proper amplification has been verified, the PCR product (20–100 μl) is digested using the TaqI restriction enzyme in the appropriate buffer for 2 hours at 65° C. Following digestion, 10 μl of the sample is run on a size fractionating gel with appropriate marker lanes and visualized. When the F3/R3 primer pair is used in the above method, two types of results are evident:

1) the absence of digestion (i.e. a 287 bp single band) which correlates with an increased risk for Seronegative Spondyloarthropathies; or 2) the presence of digestion (i.e., 2 bands; 225 bp and 62 bp in size) which indicates the presence of the recognition sequence -TCGA- at positions 4494–4497 of SEQ ID NO:1 and correlates with reduced risk (susceptibility) for the seronegative spondyloarthropathies.

In B27 negative individuals, amplification of cDNA using the primer pair F3/R3 fails to yield any product and correlates with the absence of the B27 gene.

While the invention has been described in detail with reference to certain preferred embodiments thereof, it will be understood that modifications and variations are within the spirit and scope of that which is described and claimed.

That which is claimed is:

1. A method for diagnosing a genetic predisposition in a subject for a seronegative spondyloarthropathy (ies), comprising
   obtaining a biological sample from a subject;
   determining the identity of a nucleotide present in the subject's nucleic acid at a position corresponding to nucleotide 4495 of SEQ ID NO:1 of the 3' flanking region of an HLA-B gene present in the sample or its complementary sequence; and
   diagnosing a genetic predisposition of the subject to develop a seronegative spondyloarthropathy (ies), if the nucleotide present at that position is other than a cytosine for SEQ ID NO 1 of cytosine's complementary nucleotide for the sequence complementary to SEQ. ID NO:1.

2. The method of claim 1, wherein the determination of the nucleotide present at nucleotide 4495 of SEQ ID NO:1 or its complementary sequence is accomplished by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP), and direct sequencing.

3. The method of claim 1, further comprising detecting the absence of the nucleotide sequence -TCGA- in the 3' flanking region of an HLA-B-locus gene located within about 2 kilobases of the HLA-B 3' untranslated region.

4. The method of claim 3, further comprising detecting the presence in the sample of a transcribed mRNA sequence comprising nucleotide 4112–4556 of SEQ ID NO:1, its complementary sequence or fragment thereof.

5. The method of claim 4, wherein the detection of the transcribed sequence comprises
   a) contacting nucleic acid obtained from the biological sample with primers that hybridize to nucleotide vicinal to a nucleic acid fragment of SEQ ID NO:1 comprising nucleotide 4495 of SEQ ID NO:1 or the sequence complementary thereto;
   b) amplifying any nucleotide fragment present in the subject's nucleic acid which hybridizes to the primers under conditions effective to form a detectable amplification product;
   c) determining whether the amplification product is susceptible to digestion by Taq I restriction enzyme; and
   d) taking the absence of digestion as an indication that the subject has a genetic predisposition for a seronegative spondyloarthropathy (ies).

6. The method of claim 5, wherein each primer comprises an oligonucleotide which hybridizes to nucleotides 4112–4556 of SEQ ID NO:1, its complementary sequence or fragment thereof.

7. The method of claim 6, wherein primers are at least 5 nucleotides in length.

8. The method of claim 7, wherein the primers are at least 10 nucleotides in length.

9. The method of claim 8, wherein primers are at least 15 nucleotides in length.

10. The method of claim 9, wherein the primers are at least 20 nucleotides in length.

11. The method of claim 1, wherein the nucleic acid comprises genomic DNA, cDNA, mRNA or total RNA.

12. The method of claim 11, wherein the nucleic acid comprises cDNA.

13. The method of claim 5, wherein the primers are selected from the group consisting of F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), GRAIL-R (SEQ ID NO:8) and sequences complementary thereto.

14. The method of claim 5, wherein the primers comprise primer pairs selected from the group consisting of R2 (SEQ. ID NO: 5)/F2 (SEQ. ID NO: 4), R2 (SEQ. ID NO: 5)/F3 (SEQ. ID NO: 2), R3 (SEQ. ID NO.: 3)/F2 (SEQ. ID NO: 4), R3 (SEQ. ID NO.: 3)/F3 (SEQ. ID NO: 2), R4 (SEQ. ID NO.: 7)/F2 (SEQ. ID NO: 4), R4 (SEQ. ID NO.: 7)/F3 (SEQ. ID NO: 2), F4 (SEQ. ID NO: 6)/R2 (SEQ. ID NO: 5), F4 (SEQ. ID NO: 6)/R3 (SEQ. ID NO: 3), F4 (SEQ. ID NO:6)/R4 (SEQ. ID NO: 7), F2 (SEQ. ID NO: 4)/GRAIL-R (SEQ. ID NO.: 8), F3 (SEQ. ID NO: 2)/GRAIL-R (SEQ. ID NO.: 8), F4 (SEQ. ID NO: 6)/ GRAIL-R (SEQ. ID NO: 8) and pairs of sequences complementary thereto.

15. The method of claim 1, wherein the subject is a blood relation of a subject previously diagnosed as having a seronegative spondyloarthropathy.

16. The method of claim 1, wherein the subject had previously been determined to be positive for a B27 allele.

17. The method of claim 1, for determining a genetic disposition for a seronegative spondyloarthropathy selected from the group consisting of ankylosing spondylitis, Reiter's Syndrome, reactive arthritis, psoriatic arthritis, uveitis, juvenile chronic arthritis, and arthritis associated with inflammatory bowel disease.

18. The method of claim 3, wherein the 3' flanking region of the HLA-B-locus gene
   is an RNA or cDNA segment; and
   comprises nucleotide 4112–4556 of SEQ ID NO:1 or its complementary sequence.

19. The method of claim 3, wherein the 3' flanking region of the HLA-B-locus gene
   is RNA or cDNA segment; and
   comprises nucleotide 4270–4556 of SEQ ID NO:1 or its complementary sequence.

20. An isolated nucleic acid of up to 445 nucleotide, useful for diagnosing a predisposition to a seronegative spondyloarthropathy (ies), comprising
   at least 5 contiguous nucleotide of a nucleic acid segment which specifically hybridizes to nucleotide 4112–4556 of SEQ ID NO:1 or to its complementary sequence, the nucleic acid segment being selected from the group consisting of oligonucleotides represented by the formula N through N+4, wherein N represents any one of nucleotide 4112 through 4552 of SEQ ID NO:1 and nucleotides 4116 through 4556 of the sequence complementary to SEQ ID NO:1.

21. The isolated nucleic acid of claim 20, wherein the nucleic acid segment is selected from the group of oligonucleotides represented by the formula N through N+9, wherein N represents any one of nucleotide 4112 through 4547 of SEQ ID NO:1 and 4120 through 4556 of the sequence complementary to SEQ. ID NO:1.

22. The isolated nucleic acid of claim 21, wherein the nucleic acid segment is selected from the group of oligonucleotides represented by the formula N through N+14, wherein N represents any one of nucleotide 4112 through 4542 of SEQ ID NO:1 and 4126 through 4556 of the sequence complementary to SEQ. ID NO:1.

23. The isolated nucleic acid of claim 22, wherein the nucleic acid segment is selected from the group of oligonucleotides represented by the formula N through N+19, wherein N represents any one of nucleotide 4112 through 4537 of SEQ ID NO:1 and 4131 through 4556 of the sequence complementary to SEQ. ID NO:1.

24. The isolated nucleic acid of claim 23, wherein the nucleic acid segment is selected from the group of oligonucleotides represented by the formula N through N+29, wherein N represents any one of nucleotide 4112 through 4527 of SEQ ID NO:1 and 4141 through 4556 of the sequence complementary to SEQ. ID NO:1.

25. The nucleic acid of claim 20, wherein the nucleic acid segment is selected from the group consisting of F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), and GRAIL-R (SEQ ID NO:8).

26. The nucleic acid of claim 20, comprising nucleotides 4270–4556 of SEQ ID NO:1.

27. The nucleic acid of claim 26, further comprising nucleotides 4112–4269 of SEQ ID NO:1.

28. A diagnostic kit, comprising at least one nucleic acid of claim 20 contained in a packaging material.

29. A method for detecting a predisposition of a subject to seronegative spondyloarthropathies, comprising
   obtaining a biological sample from a subject;
   determining the nucleotide sequence of the 3' flanking region of an HLA-B-locus gene to assess the presence of the nucleotide sequence -TCGA- or its complementary sequence within about 1 kilobase downstream from the end of the HLA-B 3' untranslated region of the gene; and
   taking the absence of the nucleotide sequence -TCGA- or its complementary sequence as indicative of a predisposition of the subject to develop a seronegative spondyloarthropathy (ies).

30. The method of claim 30, further comprising detecting the presence in the biological sample of a transcribed mRNA sequence comprising nucleotide 4112–4556 of SEQ ID NO:1, its complementary sequence or fragment thereof comprising 4495.

31. A method for detecting a genetic predisposition for seronegative spondyloarthropathy (ies), comprising obtaining a biological sample from a subject;

determining whether the subject is B27 positive;

determining the nucleotide sequence of the 3' flanking region of an HLA-B-locus gene to assess the presence of the nucleotide sequence -TCGA- or its complementary sequence in the nucleic acid region 3' from the B27 gene if the subject is B27 positive; and taking the absence of the nucleotide sequence -TCGA- or its complementary sequence as indicative of a predisposition of the subject to develop a seronegative spondyloarthropathy (ies).

32. A method for assessing whether or not a subject has a genetic predisposition for a seronegative spondyloarthropathy (ies), comprising contacting nucleic acid obtained from a subject suspected of having a seronegative spondyloarthropathy with primers which hybridize to nucleotide vicinal to a nucleic acid fragment comprising nucleotide 4495 of SEQ ID NO:1 or its complementary sequence;

amplifying any nucleotide fragment present in the subject's nucleic acid which hybridized to the primers under conditions effective to form a detectable amplification product; and assessing whether the thus obtained amplification product is susceptible to digestion by Taq I restriction enzyme at nucleotide 4495; and taking the absence of digestion as indicative that the subject has a genetic predisposition for developing a seronegative spondyloarthropathy.

33. The method of claim 29, wherein the determining step is conducted by assessing the presence of the nucleotide sequence which comprises nucleotide 4495 of SEQ ID NO:1 or its complementary sequence by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP), and direct sequencing.

34. The method of claim 29, wherein the absence of the nucleotide sequence -TCGA- or its complementary sequence is detected in the 3' flanking region of an HLA-B-locus gene located within about 2 kilobases of the HLA-B 3' untranslated region.

35. The method of claim 34, further comprising detecting the presence in the sample of a transcribed mRNA sequence comprising nucleotide 4112–4556 of SEQ ID NO:1, its complementary sequence or fragment thereof.

36. The method of claim 35, wherein the detection of the transcribed sequence comprises a) contacting nucleic acid obtained from the biological sample with primers that hybridize to nucleotide vicinal to a nucleic acid fragment of SEQ ID NO:1 comprising nucleotide 4495 of SEQ ID NO:1 or its complementary sequence;

b) amplifying any nucleotide fragment present in the subject's nucleic acid which hybridizes to the primers under conditions effective to form a detectable amplification product;

c) determining whether the amplification product is susceptible to digestion by Taq I restriction enzyme; and d) taking the absence of digestion as an indication that the subject has a genetic predisposition for a seronegative spondyloarthropathy (ies).

37. The method of claim 36, wherein each primer comprises an oligonucleotide which hybridizes to nucleotide 4112–4556 of SEQ ID NO:1, or its complementary sequence.

38. The method of claim 37, wherein primers are at least 5 nucleotides in length.

39. The method of claim 38, wherein the primers are at least 10 nucleotides in length.

40. The method of claim 39, wherein primers are at least 15 nucleotides in length.

41. The method of claim 40, wherein the primers are at least 20 nucleotides in length.

42. The method of claim 29, wherein the nucleic acid comprises genomic DNA, cDNA, mRNA or total RNA.

43. The method of claim 42, wherein the nucleic acid comprises cDNA.

44. The method of claim 36, wherein the primers are selected from the group consisting of F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), GRAIL-R (SEQ ID NO:8) and sequences complementary thereto.

45. The method of claim 36, wherein the primers comprise primer pairs selected from the group consisting of R2 (SEQ. ID NO: 5)/F2 (SEQ. ID NO: 4), R2 (SEQ. ID NO: 5)/F3 (SEQ. ID NO: 2), R3 (SEQ. ID NO.: 3)/F2 (SEQ. ID NO: 4), R3 (SEQ. ID NO.: 3)/F3 (SEQ. ID NO: 2), R4 (SEQ. ID NO.: 7)/F2 (SEQ. ID NO: 4), R4 (SEQ. ID NO.: 7)/F3 (SEQ. ID NO: 2), F4 (SEQ. ID NO: 6)/R2 (SEQ. ID NO: 5), F4 (SEQ. ID NO: 6)/R3 (SEQ. ID NO: 3), F4 (SEQ. ID NO: 6)/R4 (SEQ. ID NO: 7), F2 (SEQ. ID NO: 4)/GRAIL-R (SEQ. ID NO.: 8), F3 (SEQ. ID NO: 2)/GRAIL-R (SEQ. ID NO.: 8), F4 (SEQ. ID NO: 6)/ GRAIL-R (SEQ. ID NO: 8) and pairs of sequences complementary thereto.

46. The method of claim 29, wherein the subject is a blood relation of a subject previously diagnosed as having a seronegative spondyloarthropathy.

47. The method of claim 29, wherein the subject had previously been determined to be positive for a B27 allele.

48. The method of claim 29, for determining a genetic disposition for a seronegative spondyloarthropathy selected from the group consisting of ankylosing spondylitis, Reiter's Syndrome, reactive arthritis, psoriatic arthritis, uveitis, juvenile chronic arthritis, and arthritis associated with inflammatory bowel disease.

49. The method of claim 29, wherein the 3' flanking region of the HLA-B-locus gene is an RNA or cDNA segment; and comprises nucleotide 4112–4556 of SEQ ID NO:1 or a sequence complementary thereto.

50. The method of claim 34, wherein the 3' flanking region of the HLA-B-locus gene is RNA or cDNA segment; and comprises nucleotide 4270–4556 of SEQ ID NO:1 or its complementary sequence.

51. The method of claim 31, wherein the determination of the nucleotide sequence -TCGA- or its complementary sequence in the 3' region of the B27 gene is accomplished by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP), and direct sequencing.

52. The method of claim 31, wherein the absence of the nucleotide sequence -TCGA- or its complementary sequence is detected in the 3' flanking region of an HLA-B-locus gene located within about 2 kilobases of the HLA-B 3' untranslated region.

53. The method of claim 52, wherein the determining step is conducted by assessing the presence of the nucleotide sequence comprising nucleotide 4995 of SEQ ID NO:1 or its complementary sequence by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP) and direct sequencing; and the method further comprises detecting the presence in the sample of a transcribed mRNA sequence comprising nucleotide 4112–4556 of SEQ. ID NO:1, its complementary sequence or fragment thereof.

54. The method of claim 53, wherein the detection of the transcribed sequence comprises a) contacting nucleic acid obtained from the biological sample with primers that hybridize to nucleotide vicinal to a nucleic acid fragment of SEQ ID NO:1 comprising nucleotide 4495 of SEQ ID NO:1 or its complementary sequence;

b) amplifying any nucleotide fragment present in the subject's nucleic acid which hybridizes to the primers under conditions effective to form a detectable amplification product;

c) determining whether the amplification product is susceptible to digestion by Taq I restriction enzyme; and d) taking the absence of digestion as an indication that the subject has a genetic predisposition for a seronegative spondyloarthropathy (ies).

55. The method of claim 54, wherein each primer comprises an oligonucleotide which hybridizes to nucleotide 4112–4556 of SEQ ID NO:1, or its complementary sequence.

56. The method of claim 54, wherein primers are at least 5 nucleotides in length.

57. The method of claim 56, wherein the primers are at least 10 nucleotides in length.

58. The method of claim 57, wherein primers are at least 15 nucleotides in length.

59. The method of claim 58, wherein the primers are at least 20 nucleotides in length.

60. The method of claim 31, wherein the nucleic acid comprises genomic DNA, cDNA, mRNA or total RNA.

61. The method of claim 60, wherein the nucleic acid comprises cDNA.

62. The method of claim 54, wherein the primers are selected from the group consisting of F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), GRAIL-R (SEQ ID NO:8) and their complementary sequences.

63. The method of claim 54, wherein the primers comprise primer pairs selected from the group consisting of R2 (SEQ. ID NO: 5)/F2 (SEQ. ID NO: 4), R2 (SEQ. ID NO: 5)/F3 (SEQ. ID NO: 2), R3 (SEQ. ID NO.: 3)/F2 (SEQ. ID NO: 4), R3 (SEQ. ID NO.: 3)/F3 (SEQ. ID NO: 2), R4 (SEQ. ID NO.: 7)/F2 (SEQ. ID NO: 4), R4 (SEQ. ID NO.: 7)/F3 (SEQ. ID NO: 2), F4 (SEQ. ID NO: 6)/R2 (SEQ. ID NO: 5), F4 (SEQ. ID NO: 6)/R3 (SEQ. ID NO: 3), F4 (SEQ. ID NO: 6)/R4 (SEQ. ID NO: 7), F2 (SEQ. ID NO: 4)/GRAIL-R (SEQ. ID NO.: 8), F3 (SEQ. ID NO: 2)/GRAIL-R (SEQ. ID NO.: 8), F4 (SEQ. ID NO: 6)/ GRAIL-R (SEQ. ID NO: 8) and pairs of sequences complementary thereto.

64. The method of claim 31, wherein the subject is a blood relation of a subject previously diagnosed as having a seronegative spondyloarthropathy.

65. The method of claim 31, wherein the subject had previously been determined to be positive for a B27 allele.

66. The method of claim 31, for determining a genetic disposition for a seronegative spondyloarthropathy selected from the group consisting of ankylosing spondylitis, Reiter's Syndrome, reactive arthritis, psoriatic arthritis, uveitis, juvenile chronic arthritis, and arthritis associated with inflammatory bowel disease.

67. The method of claim 53, wherein the 3' flanking region of the HLA-B- locus gene is an RNA or cDNA segment; and comprises nucleotide 4112–4556 of SEQ ID NO:1 or a sequence complementary thereto.

68. The method of claim 31, wherein the 3' flanking region of the HLA-B- locus gene is RNA or cDNA segment; and comprises nucleotide 4270–4556 of SEQ ID NO:1 or its complementary sequence.

69. The method of claim 32, wherein the determination of the nucleotide sequence -TCGA- or its complementary sequence in the 3' region of hte B27 gene is accomplished by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP), and direct sequencing.

70. The method of claim 32, wherein the absence of the nucleotide sequence -TCGA- or its complementary sequence is detected in the 3' flanking region of an HLA-B-locus gene located within about 2 kilobases of the HLA-B 3' untranslated region.

71. The method of claim 70, wherein the determining step is conducted by assessing the presence of the nucleotide sequence comprising nucleotide 4995 of SEQ ID NO:1 or its complementary sequence by a method selected from the group consisting of PCR-RFLP, ligase chain reaction (LCR), oligotyping using Sequence Specific Primers (SSP), oligotyping using Sequence Specific Oligonucleotide Probes (SSOP), Single-stranded conformation polymorphism (SSCP), and direct sequencing; and the method further comprises detecting the presence in the sample of a transcribed mRNA sequence comprising nucleotide 4112–4556 of SEQ ID NO:1, its complementary sequence or fragment thereof.

72. The method of claim 71, wherein the detection of the transcribed sequence comprises a) contacting nucleic acid obtained from the biological sample with primers that hybridize to nucleotide vicinal to a nucleic acid fragment of SEQ ID NO:1 comprising nucleotide 4495 of SEQ ID NO:1 or its complementary sequence;

b) amplifying any nucleotide fragment present in the subject's nucleic acid which hybridizes to the primers under conditions effective to form a detectable amplification product;

c) determining whether the amplification product is susceptible to digestion by Taq I restriction enzyme; and d) taking the absence of digestion as an indication that the subject has a genetic predisposition for a seronegative spondyloarthropathy (ies).

73. The method of claim 72, wherein each primer comprises an oligonucleotide which hybridizes to nucleotide 4112–4556 of SEQ ID NO:1 or its complementary sequence.

74. The method of claim 72, wherein primers are at least 5 nucleotides in length.

75. The method of claim 74, wherein the primers are at least 10 nucleotides in length.

76. The method of claim 75, wherein primers are at least 15 nucleotides in length.

77. The method of claim 76, wherein the primers are at least 20 nucleotides in length.

78. The method of claim 32, wherein the nucleic acid comprises genomic DNA, cDNA, mRNA or total RNA.

79. The method of claim 78, wherein the nucleic acid comprises cDNA.

80. The method of claim 72, wherein the primers are selected from the group consisting of F3 (SEQ ID NO:2), R3 (SEQ ID NO:3), F2 (SEQ ID NO:4), R2 (SEQ ID NO:5), F4 (SEQ ID NO:6), R4 (SEQ ID NO:7), GRAIL-R (SEQ ID NO:8) and sequences complementary thereto.

81. The method of claim 72, wherein the primers comprise primer pairs selected from the group consisting of R2 (SEQ. ID NO: 5)/F2 (SEQ. ID NO: 4), R2 (SEQ. ID NO: 5)/F3 (SEQ. ID NO: 2), R3 (SEQ. ID NO.: 3)/F2 (SEQ. ID NO: 4), R3 (SEQ. ID NO.: 3)/F3 (SEQ. ID NO: 2), R4 (SEQ. ID NO.: 7)/F2 (SEQ. ID NO: 4), R4 (SEQ. ID NO.: 7)/F3 (SEQ. ID NO: 2), F4 (SEQ. ID NO: 6)/R2 (SEQ. ID NO: 5), F4 (SEQ. ID NO: 6)/R3 (SEQ. ID NO: 3), F4 (SEQ. ID NO: 6)/R4 (SEQ. ID NO: 7), F2 (SEQ. ID NO: 4)/GRAIL-R (SEQ. ID NO.: 8), F3 (SEQ. ID NO: 2)/GRAIL-R (SEQ. ID NO.: 8), F4 (SEQ. ID NO: 6)/ GRAIL-R (SEQ. ID NO: 8) and pairs of sequences complementary thereto.

82. The method of claim 32, wherein the subject is a blood relation of a subject previously diagnosed as having a seronegative spondyloarthropathy.

83. The method of claim 32, wherein the subject had previously been determined to be positive for a B27 allele.

84. The method of claim 32, for determining a genetic disposition for a seronegative spondyloarthropathy selected from the group consisting of ankylosing spondylitis, Reiter's Syndrome, reactive arthritis, psoriatic arthritis, uveitis, juvenile chronic arthritis, and arthritis associated with inflammatory bowel disease.

85. The method of claim 71, wherein the 3' flanking region of the HLA-B-locus gene is an RNA or cDNA segment; and comprises nucleotide 4112–4556 of SEQ ID NO:1 or its complementary sequence.

86. The method of claim 71, wherein the 3' flanking region of the HLA-B- locus gene is RNA or cDNA segment; and comprises nucleotide 4270–4556 of SEQ ID NO:1 or its complementary sequence.

* * * * *

UNITED STATES PATENT AND TRADEMARK OFFICE
CERTIFICATE OF CORRECTION

PATENT NO. : 5,753,442
DATED : May 19, 1998
INVENTOR(S) : Dolly B. Tyan

It is certified that error appears in the above-identified patent and that said Letters Patent is hereby corrected as shown below:

Column 2, line 14, after "(Suppl)" delete "L".

Column 4, line 10, change "generally" to --genetically--.

Column 4, line 23, after "has" insert --a--.

Column 4, line 27, change "normals" to --normal subjects--.

Column 8, line 15, after "include" insert a space.

Column 11, line 37, change "ng/gl" into --ng/µl--.

Column 16, lines 17-18, in the first instance, change "3α" into --3'--, and in the second instance, change "3α" into --3'--.

Column 16, line 25, change "EXAMPLES" into --EXAMPLE--.

Column 17, line 18, change "227" into --B27--.

Column 19, lines 23, fourth column of the Table, change "14" into --I4--, at line 24, change "13" into --I3-- and at line 25, change "12" into --I2--.

Column 20, line 7, change "67i" into --(67%--.

Column 21, line 4 of Table 7, move the asterisk from column 4 over to column 5; still column 21, delete line 10 beginning with "B*2073.

Column 26, line 1, change "paris" into --pairs--.

UNITED STATES PATENT AND TRADEMARK OFFICE
CERTIFICATE OF CORRECTION

PATENT NO. : 5,753,442
DATED : May 19, 1998
INVENTOR(S) : Dolly B. Tyan

It is certified that error appears in the above-identified patent and that said Letters Patent is hereby corrected as shown below:

Column 33, line 67, change "SEQ ID NO 1 of" into --SEQ. ID NO: 1 or--.

Column 34, line 65, after "TCGA-" insert --or its complementary sequence--.

Column 36, line 44, change "claim 20" into --claim 22--.

Column 36, line 47, delete "and".

Column 36, line 50, after "NO:1" insert --or its complementary sequences--.

Column 36, line 52, after "NO:1" insert --or its complementary sequences--.

Column 36, line 55, change "29" into --30--.

Column 37, line 1, change "30" into --29--.

UNITED STATES PATENT AND TRADEMARK OFFICE
CERTIFICATE OF CORRECTION

PATENT NO. : 5,753,442
DATED : May 19, 1998
INVENTOR(S) : Dolly B. Tyan

It is certified that error appears in the above-identified patent and that said Letters Patent is hereby corrected as shown below:

Column 37, line 39, change "29" into --30--.

Column 37, line 48, change "29" into --30--.

Column 38, line 18, change "29" into --30--.

Column 38, line 39, change "29" into --30--.

Column 38, line 42, change "29" into --30--.

Column 38, line 44, change "29" into --30--.

Column 38, line 50, change "29" into --30--

Signed and Sealed this

Twenty-second Day of June, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 6553 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:1:

```
GAATTCTAAT  CATTCAGGGA  TTACCAATAT  TGTGCTACCT  ACTGTATTAA  TAAACAAAAA      60

GGAAACTGGT  CTCTATGAGA  ATCTCTGTGT  GGTGGCTTCA  GACAAAACTT  CGCCAGGTTT     120

AGAGAGAAAA  CCCCTGTCTC  TACACCTCCA  TTCCCAGGGC  GAGCTCACTC  TCTGGCATCA     180

AGTTCTCCGT  GATCAGTTTC  CCTACACAAG  ATCCAAGAGG  AGAGGTAAGG  AGTGAGAGGC     240

AGGGAGTCCA  GTTCAGGGAC  AGGGATTCCA  GGAGGAGAAG  TGAAGGGGAA  GCGGGTGGGC     300

GCAGCCTGGG  GGTCTCTCCC  TGGTTTCCAC  AGACAGATCC  TTGTGCCGGA  CTCAGGCAGA     360

CAGTGTGACA  AAGAGGCTGG  TGTAGGAGAA  GAGGGATCAG  GACGAAGTCC  CAGGCCCCGG     420

GCGGGGCTCT  CAGGGTCTCA  GGCTCCGAGA  GCCTTGTCTG  CATTGGGGAG  GCGCAGCATT     480

GGGGATTCCC  CACTCCCACG  AGTTTCACTT  CTTCTCCCAA  CCTATGTCGG  GTCCTTCTTC     540

CAGGATACTC  GTGACGCGTC  CCCATTTCCC  ACTCCCATTG  GGTGTCGGGT  GTCTAGAGAA     600

GCCAATCAGT  GTCGCCGGGG  TCCCAGTTCT  AAAGTCCCCA  CGCACCCACC  CGGACTCAGA     660

ATCTCCTCAG  ACGCCGAGAT  GCGGGTCACG  GCGCCCCGAA  CCCTCCTCCT  GCTGCTCTGG     720
```

```
GGGGCAGTGG  CCCTGACCGA  GACCTGGGCT  GGTGAGTGCG  GGGTCGGCAG  GGAAATGGCC   780
TCTGTGGGGA  GGAGCGAGGG  GACCGCAGGC  GGGGGCGCAG  GACCCGGGGA  GCCGCGCCGG   840
GAGGAGGGTC  GGGCGGGTCT  CAGCCCCTCC  TCGCCCCAG   GCTCCCACTC  CATGAGGTAT   900
TTCCACACCT  CCGTGTCCCG  GCCCGGCCGC  GGGGAGCCCC  GCTTCATCAC  CGTGGGCTAC   960
GTGGACGACA  CGCTGTTCGT  GAGGTTCGAC  AGCGACGCCG  CGAGTCCGAG  AGAGGAGCCG  1020
CGGGCGCCGT  GGATAGAGCA  GGAGGGGCCG  GAGTATTGGG  ACCGGGAGAC  ACAGATCTGC  1080
AAGGCCAAGG  CACAGACTGA  CCGAGAGGAC  CTGCGGACCC  TGCTCCGCTA  CTACAACCAG  1140
AGCGAGGCCG  GTGAGTGACC  CCGGCCCGGG  GCGCAGGTCA  CGACTCCCCA  TCCCCACGT   1200
ACGGCCCGGG  TCGCCCCGAG  TCTCCGGGTC  CGAGATCCGC  CCCCGAGGCC  GCGGGACCCG  1260
CCCAGACCCT  CGACCGGCGA  GAGCCCCAGG  CGCGTTTACC  CGGTTTCATT  TTCAGTTGAG  1320
GCCAAAATCC  CCGCGGGTTG  GTCGGGGCGG  GGCGGGGCTC  GGGGGGACGG  GGCTGACCGC  1380
GGGGGGACGG  GGCCAGGGTC  TCACACCCTC  CAGAATATGT  ATGGCTGCGA  CGTGGGGCCG  1440
GACGGGCGCC  TCCTCCGCGG  GTACCACCAG  GACGCCTACG  ACGGCAAGGA  TTACATCGCC  1500
CTGAACGAGG  ACCTGAGCTC  CTGGACCGCC  GCGGACACGG  CGGCTCAGAT  CACCCAGCGC  1560
AAGTGGGAGG  CGGCCCGTGT  GGCGGAGCAG  CTGAGAGCCT  ACCTGGAGGG  CGAGTGCGTG  1620
GAGTGGCTCC  GCAGATACCT  GGAGAACGGG  AAGGAGACGC  TGCAGCGCGC  GGGTACCAGG  1680
GGCAGTGGGG  AGCCTTCCCC  ATCTCCTATA  GGTCGCCGGG  GATGGCCTCC  CACGAGAAGA  1740
GGAGGAAAAT  GGGATCAGCG  CTAGAATGTC  GCCCTCCCTT  GAATGGAGAA  TGGCATGAGT  1800
TTTCCTGAGT  TTCCTCTGAG  GGCCCCCTCT  TCTCTCTAGG  ACAATTAAGG  GATGACGTCT  1860
CTGAGGAAAT  GGAGGGGAAG  ACAGTCCCTA  GAATACTGAT  CAGGGGTCCC  CTTTGACCCC  1920
TGCAGCAGCC  TTGGGAACCG  TGACTTTTCC  TCTCAGGCCT  TGTTCTCTGC  CTCACACTCA  1980
GTGTGTTTGG  GGCTCTGATT  CCAGCACTTC  TGAGTCACTT  TACCTCCACT  CAGATCAGGA  2040
GCAGAAGTCC  CTGTTCCCCG  CTCAGAGACT  CGAACTTTCC  AATGAATAGG  AGATTATCCC  2100
AGGTGCCTGC  GTCCAGGCTG  GTGTCTGGGT  TCTGTGCCCC  TTCCCCACCC  CAGGTGTCCT  2160
GTCCATTCTC  AGGCTGGTCA  CATGGGTGGT  CCTAGGGTGT  CCCATGAGAG  ATGCAAAGCG  2220
CCTGAATTTT  CTGACTCTTC  CCATCAGACC  CCCCAAAGAC  ACACGTGACC  CACCACCCCA  2280
TCTCTGACCA  TGAGGCCACC  CTGAGGTGCT  GGGCCCTGGG  CTTCTACCCT  GCGGAGATCA  2340
CACTGACCTG  GCAGCGGGAT  GGCGAGGACC  AAACTCAGGA  CACTGAGCTT  GTGGAGACCA  2400
GACCAGCAGG  AGATAGAACC  TTCCAGAAGT  GGGCAGCTGT  GGTGGTGCCT  TCTGGAGAAG  2460
AGCAGAGATA  CACATGCCAT  GTACAGCATG  AGGGGCTGCC  GAAGCCCCTC  ACCCTGAGAT  2520
GGGGTAAGGA  GGGGGATGAG  GGGTCATATC  TCTTCTCAGG  GAAAGCAGGA  GCCCTTCAGC  2580
AGGGTCAGGG  CCCCTCATCT  TCCCTTCCTT  TCCAGAGCC   GTCTTCCCAG  TCCACCGTCC  2640
CCATCGTGGG  CATTGTTGCT  GGCCTGGCTG  TCCTAGCAGT  TGTGGTCATC  GGAGCTGTGG  2700
TCGCTGCTGT  GATGTGTAGG  AGGAAGAGCT  CAGGTAGGGA  AGGGGTGAGG  GGTGGGGTCT  2760
GAGTTTTCTT  GTCCCACTGG  GGGTTTCAAG  CCCCAGGTAG  AAGTGTTCCC  TGCCTCATTA  2820
CTGGGAAGCA  GCATCCACAC  AGGGGCTAAC  GCAGCCTGGG  ACCCTGTGTG  CCAGCACTTA  2880
CTCTTTTGTG  CAGCACATGT  GACAATGAAG  GACGGATGTA  TCACCTTGGT  GGTTGTGGTG  2940
TTGGGGTCCT  GATTCCAGCA  TTCATGAGTC  AGGGGAAGGT  CCCTGCTAAG  GACAGACCTT  3000
AGGAGGGCAG  TTGGTCCAGG  ACCCACACTT  GCTTTCCTCG  TGTTTCCTGA  TCCTGCCTTG  3060
GGTCTGTAGT  CATACTTCTG  GAAATTCCTT  TTGGGTCCAA  GACGAGGAGG  TTCCTCTAAG  3120
```

```
ATCTCATGGC CCTGCTTCCT CCCAGTCCCC TCACAGGGCA TTTTCTTCCC ACAGGTGGAA      3180
AAGGAGGGAG CTACTCTCAG GCTGCGTGTA AGTGATGGGG GTGGGAGTGT GGAGGAGCTC      3240
ACCCACCCCC TAATTCCTCC TGTCCCACGT CTCCTGCGGG CTCTGACCAG GTCCTGTTTT      3300
TGTTCTACTC CAGGCAGCGA CAGTGCCCAG GGCTCTGATG TGTCTCTCAC AGCTTGAAAA      3360
GGTGAGATTC TTGGGGTCTA GAGTGGGTGG GGTGGCAGGT CTGGGGGTGG GTGGGCAGT       3420
GGGGAAAGGC CTGGGTAATG GAGATTCTTT GATTGGGATG TTTCGCGTGT GTGGTGGGCT      3480
GTTAGACTG TCATCACTTA CCATGACTAA CCAGAATTTG TTCATGACTG TTGTTTTCTG       3540
TAGCCTGAGA CAGCTGTCTT GTGAGGGACT GAGATGCAGG ATTTCTTCAC GCCTCCCCTT      3600
TGTGACTTCA AGAGCCTCTG GCATCTCTTT CTGCAAAGGC ACCTGAATGT GTCTGCGTCC      3660
CTGTTAGCAT AATGTGAGGA GGTGGAGAGA CCAGCCCACC CCCGTGTCCA CTGTGACCCC     3720
TGTTCCCATG CTGACCTGTG TTTCCTCCCC AGTCATCTTT CCTGTTCCAG AGAGGTGGGG      3780
CTGGATGTCT CCATCTCTGT CTCAACTTTA TGTGCACTGA GCTGCAACTT CTTACTTCCC     3840
TACTGAAAAT AAGAATCTGA ATATAAATTT GTTTCTCAA ATATTTGCTA TGAGAGGTTG       3900
ATGGATTAAT TAAATAAGTC AATTCCTGGA ATTGAGAGA GCAAATAAAG ACCTGAGAAC       3960
CTTCCAGAAT CTGCATGTTC GCTGTGCTGA GTCTGTTGCA GGTGGGGTGT GGAGAAGGCT     4020
GTGGGGGGCC GAGTGTGGAC GGGGCCTGTG CCCATTGGT GTTGAGTCCA TCATGGGCTT      4080
TATGTGGTTA GTCCTCAGCT GGGTCACCTT CACTGCTCCA TTGTCCTTGT CCCTTCAGTG      4140
GAAACTTGTC CAGCGGGAGC TGTGACCACA GAGGCTCACA CATCGCCCTG GCGGCCCCT     4200
GCACACGGGG GTCTCTGTGC ATTCTGAGAC AAATTTTCAG AGCCATTCAC CTCTTGCCCT     4260
GCTTCTAGAG CTCCTTTTCT GCTCTGCTCT TCTGCCCTCT CTCCCTGCCC TGGTTCTAGT     4320
GATCTTGGTG CTGAATCCAA TCCCAACTCA TGAATCTGTA AAGCAGAGTC TAATTTAGAC     4380
TTACATTTGT CTGTGAAATT GGACCCGTCA TCAAGGACTG TTCTTTCCTG AAGAGAGAAC     4440
CTGATTGTGT GCTGCAGTGT GCTGGGGCAG GGGGTGCGGG GAGGGGGTTG CTGTAGAAAG     4500
AGGGATGGGG AGGGAGGGCA CACAAGCAGC ACTGCTGAGA AAAACATAGG CGGCCTCTAT     4560
CTCAGTGTGA GGGGTCCTTG TGCTGTAGCT GCCACAAAAC AGCACTTGGC CTGAGGCTAT     4620
GTTAATAAAG ATACTGCCTT CAAAATAGGG AGGTGCTCTA CAGTGATCAT TCATTCAACT     4680
GACCTTTGTC ATTGGCCAGA CATAGGACAG AATGGTTCTG CATCTGGGGA ACACCACTGA     4740
AGTAAAATCA GAAAAATCTC TGGCCTTTTG TAGCATATGT TCCAGTGGGA AGAGGCAGAC     4800
GATAGATACA CTATAACCAG AGTAAGGAAG GAAAGTGCTA GAAGGTGGTA AGTGCTGTGA     4860
GGCAGGTGAT CCAGGATGTG GGCAGTGGGG ACAGGGAAGG TGGCTGTTGT GCTGGGTAGT     4920
CAGTGTGTGC CTTGTTGCAA AGGTGACTTT TGAGGAAAGA TTTGAGAGAC ATGAGGATGT     4980
CTGGGGAAGT TCTTTCCAGG CAGAGGAAGC TCCAGTCCAA ATGCACTATG GCAGGAAGGT     5040
GTCTGTGTTC CCAGAAGAGC AAGGAGGCCA GGAGGGCTGG ACAGAGAGAA ACTGAGGTGA     5100
GGTCAGAGGT GTGGCCAGAA CAGGTGGGCT TGAGGGGAGT GGGGTTGGAT CTGGCCTTTG     5160
CTCTGAGTGG GATGGGGAGT TAGAGGACAG TTTTGAGCAG AAGAGAGCCA TGATATGACT     5220
TCTGTTTTAA AAGGATCTCT CTGACGGCTG TGCTGAGAAC AGAATTGAGA GGCGAGGGAC     5280
GAGGGAGGCA GAAGGGAAAA CAGTAGGAAT CGAGTGCAGT ATTCCAGGCT GGAGATGTCG     5340
GTTTCCTTGA CTGGGCGTG AGCAGGGGAA ATAGTGGGAC GTGAGGGGAT TCTGGATGCA     5400
TTTGAAGATG GACTCACAGC ATTTGCCAAT GGATTGTATC TGTGGTGTGA GAAAGACGAA     5460
TCAAGGACAC CCATAATTGT AAAATGAGTG AGTAGAAGGA TGGAGCTGCT GTCAGTGGAG     5520
```

| | | | | | |
|---|---|---|---|---|---|
| ATGGGGAGAC | TCTGGCAGGA | GCGTCCTGAG | GAGGGGGCAT | CACAGGCACT | CAGTGGAGGA | 5580
| GATGTCTACT | AGGAAGGCAG | GTGGGGGAGC | TGGGGTGGAA | TTTGGACAGA | CAACTCCAGA | 5640
| GTTAGGGGA | AAGGACTGGG | CTGGAGAAAT | AGATTTAGGA | GGTCACACCA | TATATATGAG | 5700
| ACTTAAAACC | TCAAGCATGG | ATGAAGCACC | AAGGGAGTGA | CTGACTATGG | AAAAGAATGA | 5760
| GCACAAGGAC | TGAACCCTGG | ACCAGTTCTA | AGGGGTGTGA | TCAGACCACA | CCCAGAGCAG | 5820
| ACTGCACAGT | TCTGGCCCCA | CGTCTAGAGG | ACACTCAGAC | AAGGAACCCC | CATGTGCACC | 5880
| AGGATCACCT | GGATGTGGTG | CTGAGATCCA | GGAAGTCTGG | AGTCGAGCAA | GAGATTCTGG | 5940
| ATTTATGACA | AGGCTGGAGC | TCATGTTGCT | GGTCTCCAGA | TCACACTTGG | AGTAGCAAGA | 6000
| ACACCAGGAT | CCCACACGTC | TGAGCATCAG | CCTCACCTCT | AGGGCTTGTC | ATATAAATGA | 6060
| TTCCTTGGTC | TTGTGCATAA | TACTCTGAGA | CAAGGGTTCT | GGGGAGTGGC | CTGTGTATTT | 6120
| TCTAAGTCCC | CACCAGCAAT | CCTATTGCTC | AGACAGATTG | GGAACCACTG | AGATCAGTGA | 6180
| TCAGAGAGTG | CCCAGGGTGG | GTGGGTGGGG | TGGGTTTTCA | AACCCTGTTG | AAAAGAGGAT | 6240
| TTTTCTCACA | GAAAGAAAAG | GGAGGATGTA | TATCATCAGT | TATGAGAGGT | GATATTCTCT | 6300
| GTTGTTCTCT | CCACCATGGG | GTAGAGGCCA | GGTAGACAAC | TCAGGATGTG | GCTCTCGCAC | 6360
| AAAGAACACC | TCTGAATGCC | GCTCTCTGAC | ACTCGCCCGC | AGACTCATTT | CTCACTCACT | 6420
| TCTTGGAGAA | AACTATGGAA | ACCAAATTTC | TGTAATGTAC | ACAGAAAGTC | GTATATCTGG | 6480
| TATTGGGGGC | TAGTTTTATT | CCGGGGAAGG | CTACAGAAGC | AGGCTGGAAA | CTACACATCC | 6540
| GGGAACAGAA | TTC | | | | | 6553

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:2:

AGGCCGCCTA TGTTTTCTC AG        22

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:3:

GCTCCTTTTC TGCTCTGCTC TTCT        24

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:4:

```
TGCCCTCCCT CCCCATCCCT C                                                              21
```

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:5:

```
ACGGGGGTCT CTGTGCATTC TGA                                                            23
```

( 2 ) INFORMATION FOR SEQ ID NO:6:

( i ) SEQUENCE CHARACTERISTICS:
    ( A ) LENGTH: 19 base pairs
    ( B ) TYPE: nucleic acid
    ( C ) STRANDEDNESS: both
    ( D ) TOPOLOGY: linear ( i i ) MOLECULE TYPE: DNA (genomic)

( x i ) SEQUENCE DESCRIPTION: SEQ ID NO:6:

```
CAACCCCTC CCCGCACCC                                                                  19
```

( 2 ) INFORMATION FOR SEQ ID NO:7:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: DNA (genomic)

( x i ) SEQUENCE DESCRIPTION: SEQ ID NO:7:

```
CTGATTGTGT GCTGCAGTGT GCTG                                                           24
```

( 2 ) INFORMATION FOR SEQ ID NO:8:

( i ) SEQUENCE CHARACTERISTICS:
    ( A ) LENGTH: 23 base pairs
    ( B ) TYPE: nucleic acid
    ( C ) STRANDEDNESS: both
    ( D ) TOPOLOGY: linear ( i i ) MOLECULE TYPE: DNA (genomic)

( x i ) SEQUENCE DESCRIPTION: SEQ ID NO:8:

```
CACTGCTCCA TTGTCCTTGT CCC                                                            23
```